United States Patent
Johnson-Terleski et al.

(10) Patent No.: US 12,138,123 B2
(45) Date of Patent: *Nov. 12, 2024

(54) UNIFIED INTERFACE FOR VISUALIZING 2D, 3D AND 4D ULTRASOUND IMAGES

(71) Applicant: yoR Labs, Inc., Portland, OR (US)

(72) Inventors: Oliver C. Johnson-Terleski, Tualatin, OR (US); Matthew C. Morrise, Portland, OR (US)

(73) Assignee: yoR Labs, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/445,690

(22) Filed: Aug. 23, 2021

(65) Prior Publication Data
US 2022/0061811 A1 Mar. 3, 2022

Related U.S. Application Data

(60) Provisional application No. 63/070,214, filed on Aug. 25, 2020.

(51) Int. Cl.
*A61B 8/00* (2006.01)
*A61B 8/08* (2006.01)

(52) U.S. Cl.
CPC ............ *A61B 8/463* (2013.01); *A61B 8/0833* (2013.01); *A61B 8/44* (2013.01); *A61B 8/467* (2013.01)

(58) Field of Classification Search
None
See application file for complete search history.

(56) References Cited

U.S. PATENT DOCUMENTS

| 4,998,132 A | 3/1991 | Kurogane |
| 5,617,371 A | 4/1997 | Williams |

(Continued)

FOREIGN PATENT DOCUMENTS

| AU | 2018250516 | 11/2018 |
| EP | 2 288 284 | 5/2016 |

(Continued)

OTHER PUBLICATIONS

Bradley, Aug. 2008, Retrospective transmit beamformation: Acuson SC2000 volume imaging ultrasound system, Siemens Medical Solutions USA, Inc., whitepaper, 8 pp.

(Continued)

*Primary Examiner* — Joel Lamprecht
*Assistant Examiner* — Ashish S Jasani
(74) *Attorney, Agent, or Firm* — Knobbe, Martens, Olson & Bear, LLP

(57) ABSTRACT

Systems and methods for visualizing two-dimensional (2D), three-dimensional (3D), and four-dimensional (4D) ultrasound images generated by an ultrasound device are disclosed. In one aspect, the method includes displaying a display state selection on a user interface of a display screen in communication with a computing device, the display state selection indicating to receive 2D or 3D images. The method further includes receiving, from the user interface, a display state user selection indicating to generate 2D or 3D images. The method further includes, in response to receiving the display state user selection, controlling the ultrasound device to generate ultrasound images of the selected display state and communicate the generated ultrasound images to the computing device. The method further includes displaying the received ultrasound images on a portion of the display screen.

17 Claims, 24 Drawing Sheets

(56) References Cited

U.S. PATENT DOCUMENTS

| | | | |
|---|---|---|---|
| 5,903,516 A | 5/1999 | Greenleaf et al. | |
| 5,908,389 A | 6/1999 | Roundhill et al. | |
| 6,031,529 A | 2/2000 | Migos | |
| 6,063,030 A | 5/2000 | Vara et al. | |
| 6,120,450 A | 9/2000 | Li | |
| 6,123,670 A | 9/2000 | Mo | |
| 6,132,374 A | 10/2000 | Hossack et al. | |
| 6,400,981 B1 | 6/2002 | Govari | |
| 6,607,489 B2 | 8/2003 | Hoctor | |
| 6,690,963 B2 | 2/2004 | Haim et al. | |
| 6,908,434 B1 | 6/2005 | Jenkins et al. | |
| 7,090,639 B2 | 8/2006 | Govari | |
| 7,423,578 B1 | 9/2008 | Tietjen | |
| 7,604,601 B2 | 10/2009 | Altmann et al. | |
| 7,648,462 B2 | 1/2010 | Jenkins et al. | |
| 7,667,639 B2 | 2/2010 | Cheng et al. | |
| 7,682,358 B2 | 3/2010 | Gullickson et al. | |
| 7,750,849 B2 | 7/2010 | Hjelmstad | |
| 7,831,076 B2 | 11/2010 | Altmann et al. | |
| 7,860,553 B2 | 12/2010 | Govari et al. | |
| 7,918,793 B2 | 4/2011 | Altmann et al. | |
| 7,996,060 B2 | 8/2011 | Trofimov et al. | |
| 8,075,486 B2 | 12/2011 | Tal | |
| 8,285,364 B2 | 10/2012 | Barbagli et al. | |
| 8,390,438 B2 | 3/2013 | Olson et al. | |
| 8,449,467 B2 | 5/2013 | Wilser et al. | |
| 8,517,946 B2 | 8/2013 | Kim | |
| 8,676,290 B2 | 3/2014 | Tegg | |
| 8,690,871 B2 | 4/2014 | Partlett et al. | |
| 8,702,612 B2 | 4/2014 | Hendriks et al. | |
| 8,989,842 B2 | 3/2015 | Li et al. | |
| 9,030,354 B2 | 5/2015 | Natarajan | |
| 9,055,883 B2 | 6/2015 | Tgavalekos et al. | |
| 9,095,682 B2 | 8/2015 | Romoscanu | |
| 9,132,913 B1 | 9/2015 | Shapiro et al. | |
| 9,179,890 B2 | 11/2015 | Ionasec et al. | |
| 9,211,160 B2 | 12/2015 | Pivotto et al. | |
| 9,261,595 B2 | 2/2016 | Garbini et al. | |
| 9,323,445 B2 | 4/2016 | Kritt et al. | |
| 9,342,156 B2 | 5/2016 | Huh | |
| 9,922,554 B2 | 3/2018 | Mikuni et al. | |
| 9,931,487 B2 | 4/2018 | Quinn et al. | |
| 9,986,969 B2 | 6/2018 | Call et al. | |
| 10,183,149 B2 | 1/2019 | Tegg et al. | |
| 10,206,652 B2 | 2/2019 | Deno et al. | |
| 10,368,951 B2 | 8/2019 | Moll et al. | |
| 10,401,492 B2 | 9/2019 | Brooks | |
| 10,405,830 B2 | 9/2019 | Garbini et al. | |
| 10,463,439 B2 | 11/2019 | Joseph et al. | |
| 10,499,882 B2 * | 12/2019 | Hunter | A61B 8/465 |
| 10,537,307 B2 | 1/2020 | Yang | |
| 10,555,780 B2 | 2/2020 | Tanner et al. | |
| 10,624,612 B2 | 4/2020 | Sumi | |
| 11,344,281 B2 | 5/2022 | Morisse et al. | |
| 11,547,386 B1 | 1/2023 | Roy et al. | |
| 2002/0173721 A1 | 11/2002 | Grunwald | |
| 2002/0173722 A1 | 11/2002 | Hoctor et al. | |
| 2003/0007598 A1 | 1/2003 | Wang et al. | |
| 2003/0055334 A1 | 3/2003 | Steinbacher et al. | |
| 2003/0055337 A1 | 3/2003 | Lin | |
| 2004/0102700 A1 | 5/2004 | Asafusa | |
| 2005/0288588 A1 | 12/2005 | Weber et al. | |
| 2007/0027733 A1 | 2/2007 | Balle | |
| 2007/0174772 A1 | 7/2007 | Gorman | |
| 2007/0200760 A1 | 8/2007 | Hjelmstad | |
| 2007/0239001 A1 | 10/2007 | Mehi et al. | |
| 2007/0259158 A1 | 11/2007 | Friedman et al. | |
| 2008/0012753 A1 | 1/2008 | Cheng | |
| 2008/0114239 A1 | 5/2008 | Randall et al. | |
| 2008/0215046 A1 | 9/2008 | Messing et al. | |
| 2008/0306385 A1 | 12/2008 | Jago | |
| 2009/0043206 A1 | 2/2009 | Towfiq et al. | |
| 2009/0118620 A1 | 5/2009 | Tgavalekos et al. | |
| 2009/0271704 A1 | 10/2009 | Cohen | |
| 2010/0030076 A1 | 2/2010 | Vortman et al. | |
| 2010/0081938 A1 | 4/2010 | Kato | |
| 2010/0146431 A1 | 6/2010 | Raji et al. | |
| 2010/0160784 A1 | 6/2010 | Poland | |
| 2010/0168580 A1 | 7/2010 | Thiele | |
| 2010/0251823 A1 | 10/2010 | Adachi | |
| 2011/0077524 A1 | 3/2011 | Oshiki et al. | |
| 2011/0137132 A1 | 6/2011 | Gustafson | |
| 2011/0208052 A1 | 8/2011 | Entrekin | |
| 2012/0075208 A1 | 3/2012 | Tamiya et al. | |
| 2012/0157851 A1 | 6/2012 | Zwirn | |
| 2012/0254747 A1 | 10/2012 | Bocirnea | |
| 2013/0227052 A1 | 8/2013 | Wenzel | |
| 2013/0234891 A1 | 9/2013 | Natarajan et al. | |
| 2013/0238990 A1 | 9/2013 | Ubillos et al. | |
| 2013/0253317 A1 | 9/2013 | Gauthier | |
| 2013/0274712 A1 | 10/2013 | Schecter et al. | |
| 2014/0035916 A1 | 2/2014 | Murphy | |
| 2014/0046188 A1 | 2/2014 | Yen et al. | |
| 2014/0058266 A1 | 2/2014 | Call et al. | |
| 2014/0087342 A1 | 3/2014 | Campanatti, Jr. | |
| 2014/0164965 A1 | 6/2014 | Lee et al. | |
| 2014/0189560 A1 | 7/2014 | Caspi | |
| 2014/0219059 A1 | 8/2014 | Younghouse | |
| 2015/0019488 A1 | 1/2015 | Higginson et al. | |
| 2015/0065877 A1 | 3/2015 | Orderud | |
| 2015/0082251 A1 | 3/2015 | Lam | |
| 2015/0293223 A1 | 10/2015 | Park et al. | |
| 2016/0054901 A1 | 2/2016 | Yang et al. | |
| 2016/0157824 A1 | 6/2016 | Park et al. | |
| 2016/0161589 A1 | 6/2016 | Benattar | |
| 2016/0161594 A1 | 6/2016 | Benattar | |
| 2016/0161595 A1 | 6/2016 | Benattar | |
| 2016/0165338 A1 | 6/2016 | Benattar | |
| 2016/0165341 A1 | 6/2016 | Benattar | |
| 2016/0338676 A1 | 11/2016 | Berger et al. | |
| 2017/0090571 A1 | 3/2017 | Bjaerum | |
| 2017/0153801 A1 | 6/2017 | Kim et al. | |
| 2017/0307755 A1 | 10/2017 | Brooks | |
| 2017/0343655 A1 | 11/2017 | Solek et al. | |
| 2017/0343668 A1 | 11/2017 | Brooks et al. | |
| 2018/0000449 A1 | 1/2018 | Moore et al. | |
| 2018/0000453 A1 * | 1/2018 | Hunter | G06F 3/04883 |
| 2018/0055483 A1 | 3/2018 | Hunter | |
| 2018/0064415 A1 | 3/2018 | Zhai et al. | |
| 2018/0361145 A1 | 12/2018 | Mahapatra et al. | |
| 2019/0245310 A1 | 8/2019 | Medina et al. | |
| 2019/0261953 A1 | 8/2019 | Honjo et al. | |
| 2019/0307427 A1 | 10/2019 | Levy et al. | |
| 2019/0324139 A1 | 10/2019 | Brooks | |
| 2019/0353975 A1 | 11/2019 | DiDomenico | |
| 2020/0046321 A1 | 2/2020 | Duda | |
| 2020/0060646 A1 | 2/2020 | Lindenroth et al. | |
| 2020/0170662 A1 | 6/2020 | Vardi | |
| 2020/0178928 A1 | 6/2020 | Park et al. | |
| 2020/0183004 A1 | 6/2020 | Gong et al. | |
| 2020/0205783 A1 | 7/2020 | Shiran | |
| 2020/0268351 A1 | 8/2020 | Chiang | |
| 2020/0281565 A1 * | 9/2020 | Yee | A61B 8/465 |
| 2020/0315592 A1 | 10/2020 | Soleimani et al. | |
| 2021/0007710 A1 | 1/2021 | Douglas | |
| 2021/0022716 A1 * | 1/2021 | Kerby | A61B 8/469 |
| 2021/0038334 A1 | 2/2021 | Hsu et al. | |
| 2021/0125503 A1 | 4/2021 | Henry et al. | |
| 2021/0177379 A1 | 6/2021 | Kolen et al. | |
| 2021/0196237 A1 * | 7/2021 | Bellamkonda | A61B 8/463 |
| 2021/0338208 A1 | 11/2021 | Nguyen et al. | |
| 2021/0401508 A1 | 12/2021 | Zhao | |
| 2022/0061814 A1 | 3/2022 | Morrise | |
| 2022/0151591 A1 | 5/2022 | Morrise | |
| 2022/0156094 A1 | 5/2022 | Morrise | |
| 2023/0059122 A1 | 2/2023 | Pellegrino | |

FOREIGN PATENT DOCUMENTS

| | | |
|---|---|---|
| EP | 3 275 478 | 1/2018 |
| EP | 2 707 076 | 11/2018 |
| EP | 3 050 214 | 3/2019 |
| EP | 2 632 318 | 11/2019 |
| EP | 3 518 777 | 3/2021 |

(56) References Cited

FOREIGN PATENT DOCUMENTS

| WO | WO 12/088535 | 6/2012 |
| WO | WO 20/049012 | 3/2020 |
| WO | WO 20/252416 | 12/2020 |

OTHER PUBLICATIONS

Lin et al., Jun. 2010, A motion compounding technique for speckle reduction in ultrasound images, Journal of digital imaging 23(3):246-257.

* cited by examiner

Individual images each form a slice of object from different positions

Stacking slices together can be stitched to form 3D image

UNIFIED INTERFACE FOR VISUALIZING 2D, 3D AND 4D ULTRASOUND IMAGES

BACKGROUND OF THE INVENTION

Field

The disclosed technology relates to systems and methods for visualizing ultrasound images. Specifically, the disclosed technology relates to a user interface for displaying a variety of ultrasound workflow states and ultrasound data representations within a single display screen. The user interface allows a user to navigate between active scanning and saved scans, and to perform a variety of transformations of ultrasound images or actions on scan data, while staying within a single display screen.

Description of the Related Art

Ultrasound imaging may be used in the diagnosis, screening, and treatment of a variety of diseases and conditions. An ultrasound image may be created by transmitting sound waves into the body and then interpreting the intensity of the reflected echoes. The echoes may be used to produce two dimensional, three-dimensional, and color flow images of internal anatomical features of objects, for example, in patients.

The state-of-the-art mobile ultrasound scanning technology generally does not function or operate under a single screen paradigm. Instead, implementations often function by segmenting active and saved workflows, treating them as distinct operations. Additionally, current technology generally does not support full 3D imaging in a mobile form factor, instead most of the imaging states are 2D displays. Therefore, most of the existing process workflows only consider the scanning mode within a 2D state where image parameters may be modified during a scan, but the image representation does not support transforming between 2D and 3D data. Once an image is captured, a user generally cannot take actions on that data, e.g., taking projections or singular frames, while leaving the original capture intact.

As the number of functions performed by ultrasound systems increases, the size and complexity of the user interface, i.e., the control panel, also increases. This complexity can make it inefficient and time consuming to acquire and optimize images and enter the data for each captured image. Every image requires at least two labels which may be typed by the sonographer using a hand that is not handling the ultrasound system. Additionally, there are a variety of measurements which the sonographer obtains by manually placing electronic calipers on the image. The process of optimizing the image, labeling, and measuring may be cumbersome, time consuming and prone to errors. There is therefore a need for an ultrasound system that provides the operator with a more streamlined method and interface for optimizing the image, labeling, and making measurements in ultrasound images.

SUMMARY

An objective of the disclosed technology is to provide solutions to the aforementioned technical problems of the state-of-the-art mobile ultrasound scanning technology. Objectives of the disclosed technology include allowing integration of active and saved workflows within a single display screen, supporting 2D and 3D imaging as well as transformation between 2D and 3D in a mobile form factor, through contextual design elements that may be displayed to and may be actionable to a user based on current state of the scan and prior selections of the user.

One innovation includes a method for visualizing two-dimensional (2D), three-dimensional (3D), and four-dimensional (4D) ultrasound images generated by a hand-held ultrasound device, the method including receiving ultrasound images generated by the hand-held ultrasound device, and displaying a display state selection on a user interface of a display screen in communication with a computing device, the display state selection indicating to receive 2D or 3D images. The method can further include receiving from the user interface a display state user selection indicating to generate 2D or 3D images, and in response to receiving the display state user selection, controlling the ultrasound device to generate ultrasound images of the selected display state and communicate the generated ultrasound images to the computing device; and displaying the generated ultrasound images on a portion of the display screen.

Various embodiments may include other features, or characterizations of the features. For example, generating ultrasound images can include generating 2D images, and the method can further include displaying a capture graphical indicator on the user interface, for capturing one of the 2D images displayed on the display screen, and in response to receiving user input selecting the capture graphical indicator, storing currently displayed 2D image. In some embodiments, generating ultrasound images includes generating 3D images, and the method can further include displaying a capture graphical indicator on the user interface, for capturing one of the 3D images displayed on the display screen, and in response to receiving user input selecting the capture graphical indicator, storing currently displayed 3D image. In some embodiments, generating ultrasound images includes generating 2D images, and wherein the method further includes displaying a 2D frozen review graphical indicator on the user interface, for reviewing a most recent portion of the 2D images generated by a hand-held ultrasound device, and in response to receiving user input selecting the 2D frozen review graphical indicator, displaying the most recent portion of the 2D images on a portion of the display screen. In some embodiments, the method further includes displaying time series of 2D images on a portion of the display screen. In some embodiments, generating ultrasound images comprises generating 3D images, and the method further includes displaying a 3D frozen review graphical indicator on the user interface, for reviewing a most recent portion of the 3D images generated by a hand-held ultrasound device, and in response to receiving user input selecting the 3D frozen review graphical indicator, displaying the most recent portion of the 3D images on a portion of the display screen. In some embodiments, the method includes comprising displaying time series of 3D images on a portion of the display screen. In some embodiments, the method further comprises displaying a 2D projection function on the user interface, for viewing 2D sections of the 3D images at a specified plane, and in response to receiving user input selecting the 2D projection function, displaying the 2D sections on a portion of the display screen. In some embodiments, the method further comprises displaying time series of the 2D sections on a portion of the display screen.

Other implementations of the method can include additional features. For example, in some embodiments the method can further comprise displaying a capture graphical indicator on the user interface, for capturing one of the ultrasound images displayed on the display screen, in response to receiving user input selecting the capture graphical indicator, storing currently displayed image as a captured image, saving the captured image to a database, and displaying a thumbnail of the captured image in a gallery on the user interface, for current examination. In some embodiments, the method further includes displaying a plurality of thumbnails of a plurality of captured images in the gallery on the user interface, and in response to receiving user input selecting one of the plurality of thumbnails in the gallery, displaying the corresponding captured image on a portion of the display screen for current examination. In some embodiments, the displayed captured image is from a 2D scan, and wherein the method further comprises displaying time series of 2D images on a portion of the display screen. In some embodiments, the displayed captured image is from a 3D scan, and wherein the method can further include displaying time series of 3D images on a portion of the display screen. In some embodiments, the method further includes displaying a 2D projection function on the user interface, for viewing 2D sections of the 3D images at a specified plane, and in response to receiving user input selecting the 2D projection function, displaying the 2D sections on a portion of the display screen. In some embodiments, the method further includes displaying time series of the 2D sections on a portion of the display screen. In some embodiments, the display screen is on a mobile device, for example, a laptop computer, a tablet computer, or a mobile telephone. In some embodiments, receiving ultrasound images further comprising importing the active ultrasound image to a touchpad on the user interface, wherein by tapping on the lesion on the touchpad, a relative depth of the lesion in an image frame of the anatomical feature is captured.

Another innovation is a method for labeling ultrasound images, comprising receiving at a computing device ultrasound images generated by a hand-held ultrasound device, displaying on a display screen, in communication with the computing device, a first active ultrasound image, displaying a proportional graphical representation of the anatomical feature on a user interface comprising a touch-screen, the displayed graphical representation being displayed separately from the first active ultrasound image displayed on the first device display screen, and detecting, from a user, a touch gesture on the user interface. The method can further include correlating the touch gesture on the user interface with a stored image manipulation function, wherein each of a plurality of touch gestures is correlated to a different image manipulation function, applying the image manipulation function associated with the touch gesture to the active ultrasound image and to the graphical representation of the anatomical feature being scanned, wherein information associated with the touch gesture on the user interface manipulates the active ultrasound image, and labeling the graphical representation of the anatomical feature with a location of a lesion or other imaged feature of interest, wherein a label applied to the graphical representation of the anatomical feature on the user interface appears on the active ultrasound image that is being displayed on the display screen, wherein subsequent touch gestures on the user interface modify the label of the lesion on the displayed active ultrasound image.

DETAILED DESCRIPTION

Overview

Figure 1A:
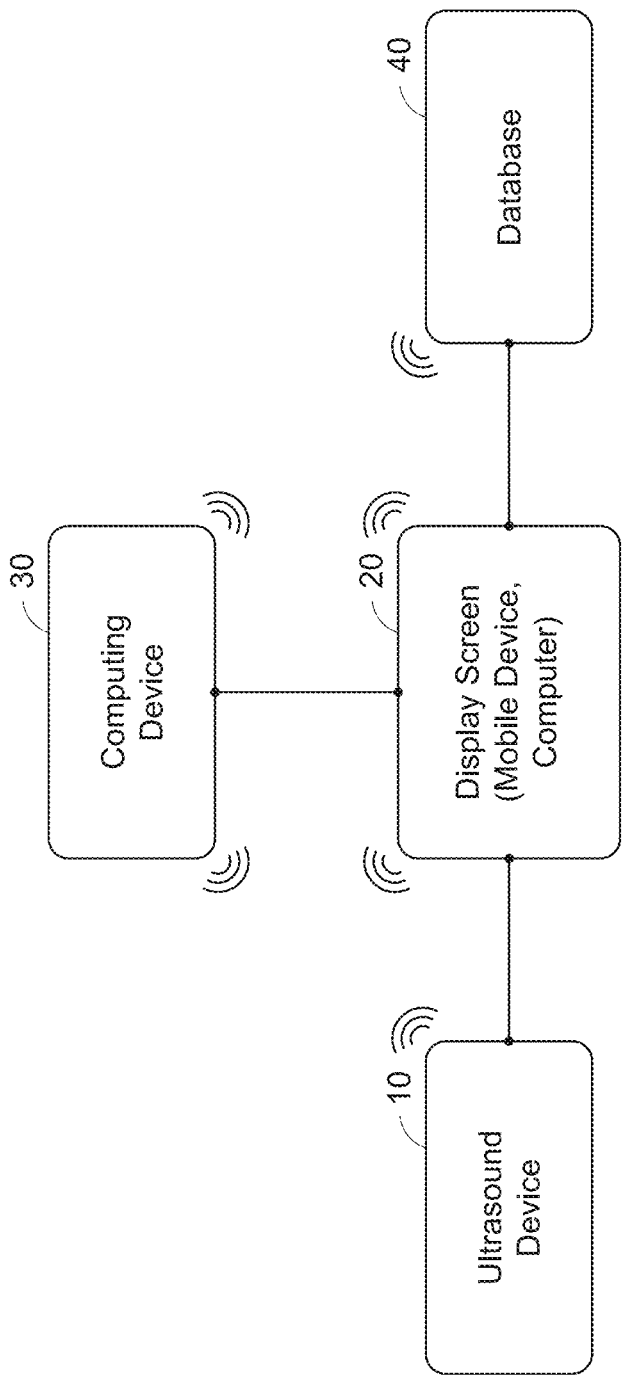
FIG. 1A is a schematic illustrating an ultrasound device connected to a display screen, a computing device, and a database, operated by a user.

Embodiments of systems and methods for visualizing two-dimensional (2D), three-dimensional (3D), and four-dimensional (4D) ultrasound images generated by a ultrasound device, e.g., a hand-held ultrasound device, within a unified user interface of a single display screen are disclosed herein.

The disclosed unified user interface allows for the following operations of the ultrasound images: When viewing 2D or 3D cineloops the user can replay the cineloop or manually scroll through the cineloop. When running the loop the user can adjust the replay speed. When displaying 3D images and cineloops the slices can be viewed all at once or one at a time, either automatically or manually. Cineloops can be saved while scanning or while frozen. 2D and 3D images can be saved from any cineloop. A cineloop can be converted to a 3D image. All saved captures may be displayed as thumbnails in a gallery. Selecting any thumbnail displays the corresponding capture for review. 2D captures can be zoomed, rotated, or moved. 3D captures can be zoomed, rotated, tilted, or moved. 3D rotation can be done using a touch screen of a tablet or mobile phone. Alternatively, 3D rotation can be done by physically orienting the tablet or mobile phone and using inertial measurement unit (IMU) values to rotate the 3D capture. A user can return to scanning at any time.

Terms

In order to facilitate an understanding of the systems and methods discussed herein, a number of terms are defined below. The terms defined below, as well as other terms used herein, should be construed to include the provided definitions, the ordinary and customary meaning of the terms, and/or any other implied meaning for the respective terms. Thus, the definitions below do not limit the meaning of these terms, but only provide exemplary definitions.

A "scanner" or "ultrasound device" in this context refers to a device for performing ultrasound imaging (sonography), which uses high-frequency sound waves to examine an object. The device may comprise an ultrasonic transducer or an ultrasonic transducer array used to probe the object. Transducers may be part of a sequential array in which the acoustic beam is focused straight in front of the transducer, providing high sensitivity but a limited field of view, or a phased array in which each transducer sends an acoustic beam in a coordinated sequence, establishing a pattern of constructive interference that results in a beam at a set angle, allowing for a wider field of view. Phased array transducers may comprise multiple transducer elements which may be arranged in a variety of shapes including a strip (linear array), a ring (annular array), a circular matrix (circular array), conformal array, curved, or a more complex shape. A "scanner" used herein may include hand-held or portable device.

A scanner transmits ultrasound signals toward a target part within an object, collects echo signals reflected from the target part, and generates an ultrasonic image. To this end, the scanner may perform "beamforming" to estimate amplitude of a reflected wave in a particular space from a plurality of channel data collected by an ultrasonic probe from the echo signals.

"Beamforming" in this context refers to an operation to focus echo signals input through multiple ultrasonic sensors, e.g., transducers, by compensating time difference of the echo signals and stressing or attenuating a signal on a particular position using a predetermined weight, i.e., a beamforming coefficient for each echo signal. After performing beamforming, the scanner may generate an ultrasonic image representing an internal structure of the object and display the ultrasonic image. Depending on characteristics of the beamforming coefficient used in beamforming, beamforming may be data-independent beamforming or adaptive. The data-independent beamforming uses a set weight regardless of the input echo signal while the adaptive beamforming determines a weight based on the input echo signal. Accordingly, the weight in the adaptive beamforming varies with input echo signals. A "beamformed" image in this context refers to an image generated with the beamforming operation.

"Ultrasound study" in this context refers to a diagnostic procedure performed by a sonographer that uses two-dimensional images produced by inaudible sound waves to evaluate an anatomical feature.

"User" in this context refers to the person performing an ultrasound scan. "Reader" in this context refers to the person interpreting an ultrasound scan. A "sonographer" may both perform and interpret an ultrasound scan.

"Scan plane" in this context refers to the orientation of the ultrasound probe relative to the part being scanned.

When 3D imaging is available, ultrasound viewing and saving may include three modes: scanning, frozen, and review. "Scanning" in this context refers to showing images directly from the scanner (e.g., the ultrasound device). "Frozen" in this context refers to showing the last N seconds of images from the scanner. "Review" in this context refers to showing images that are explicitly saved.

A "frame" in this context is for specifying the space and time aspect of an image. In other words, a frame is the image at a given position with respect to the time the image was taken. In some embodiments, a "frame" may be a 2D image. In other embodiments, when a user is performing the 3D imaging mode via an ultrasound device, a "frame" may additionally cover each image taken by the ultrasound device in that same instance.

Bundled images in frozen and review modes are called a "capture" and there are four types of capture: 2D image, 2D series (cineloop), 3D image, and 3D series (3D cineloop).

The information (or image data) that constitute ultrasound 3D image captures are called "slices." A "slice" in this context may be a thin 3D composite image formed from a collection of 2D images.

A "thick slice mode" in this context refers to a 3D image taken by an ultrasonic transducer array. A "tomography" in this context refers to a time series of 2D or 3D images taken by an ultrasonic transducer array when the ultrasonic transducer array is being moved or translated along the object being scanned.

A "loop", "cineloop", "timelapse", or "video loop" in this context may be used interchangeably to refer to a time series of images. In some embodiments, a 4D image may be a timelapse of 3D image(s). In other embodiments, individual frames can be sequenced to form a video loop.

"Database" in this context refers to an organized collection of data (states of matter representing values, symbols, or control signals to device logic), structured typically into tables that comprise 'rows' and 'columns.'

"Graphical representation" in this context refers to a stylized drawing of the body part being scanned.

"Module" in this context refers to logic having boundaries defined by function or subroutine calls, branch points, application program interfaces, or other technologies that provide for the partitioning or modularization of particular processing or control functions. Modules are typically combined via their interfaces with other modules to carry out a machine process.

"Touch screen" in this context refers to a capacitive or resistive display which responds to direct touch manipulation, either by finger (simple or multi-touch), stylus, or both. The user can use the touchscreen to react to what is displayed and to control how it is displayed. The touchscreen enables the user to interact directly with information displayed rather than using a mouse, touchpad, or other intermediate device (with the exception of a stylus).

Data Representation

In some embodiments, the data representation of a scanned image may be able to represent all the needed fields to both display and to signify the exact display variant the renderer should use. Additionally, the data format may be flexible enough to allow for transformations to other supported display variants if possible.

The data implementation may represent a single slice or a single frame, or captures which are collections of images along with other information. Checking the contents of captures allows for explicitly knowing the type of scan and variant needed to display. Knowing this type then specifies all actions that can be taken on the capture, as well as directing the display renderer how it should render the image data.

An image may be a single frame or a single slice. In some embodiments, image data that is saved to the database for an individual image may include, for example, the following immutable fields:

(1) Raw pixel data for what was imaged.
(2) Depth details to specify constraint of bottom of image. The depth refers to a 2D image's y-axis which corresponds to how deep the scanner is imaging.
(3) Timestamp to have relative timing information relative to other image data
(4) Relative position data in x, y, and z directions. The y direction may be defined as the direction normal to the ultrasonic transducer array.
(5) Relative angle position data in x, y, and z directions.

(6) Relative slice position and total number of slices for beamformed 3D image if applicable.

Bundled images in frozen and review modes are called a capture. A capture may be a 2D image, a 2D series (cineloop), a 3D image, or a 3D series (3D cineloop). A capture may include multiple frames and/or slices, where the multiple frames may include images that are changing in time, and multiple slices may include images that are changing spatially. A capture may be the full collection of the images taken over both time and space. Different capture types represent different display variants, including:

A "frame," which is a single image at a given time point.

A "loop," which include multiple images focused on essentially the same spatial area but changing in time.

A "slice," which includes images of a spatial range near a spatial position, e.g., a stack of cross-sections. Multiple slices are used to create a 3D image.

A "2D timelapse" or a 3D "timelapse," which includes images taken in the same location over a time range.

A "thick slice," which includes images taken in 3D mode in a stable location with a given spatial and time sampling rate.

A "tomography," which includes images taken while traversing (moving the scanning probe) a region that is both time and spatially variant. The relative spatial position and orientation of each individual image, which are given by the IMU value of the scanner, may be taken into account when forming a tomography based on a plurality of images.

A "loop," which is a time series of data. The spatial information can be rendered in 3D or as a 2D plane. As each image data has time and spatial information, projections between the different dimensions can be made.

Embodiments

Figure 1B:
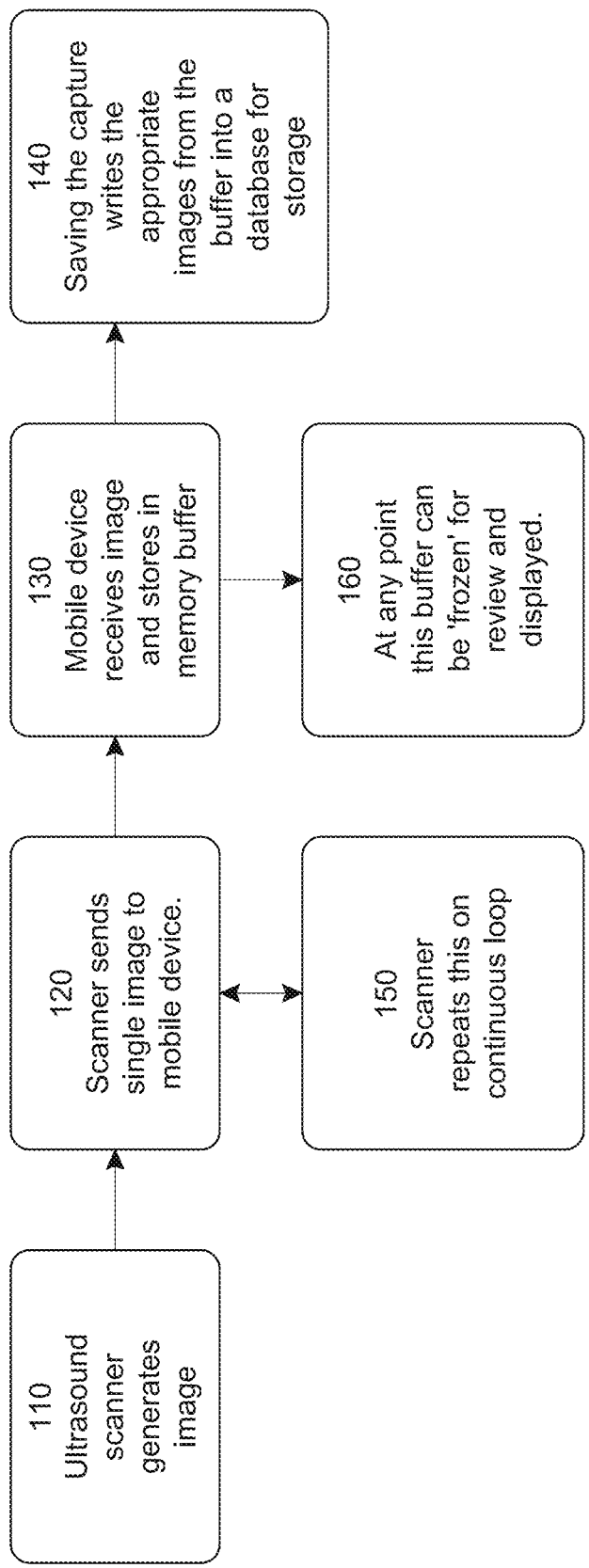
FIG. 1B illustrates an exemplary process from generating to saving ultrasound images.

FIG. 1A and FIG. 1B illustrate an exemplary process from generating ultrasound images by a scanner 10 to saving ultrasound images into a database 40. The process may start at block 110, where a user (e.g., a medical professional) uses a scanner 10 (e.g., a hand-held ultrasound device) to generate ultrasound image(s). Then, the process may move to block 120, where the scanner 10 automatically sends a single image to a mobile device (e.g., a tablet or a mobile phone), through wired or wireless communication. The process may repeat block 150, where the scanner 10 automatically sends another image to the mobile device, on a continuous loop. Accordingly, at block 130, the mobile device receives image(s) and automatically stores the received image(s) in a memory buffer. After the received image(s) has been stored in the memory buffer, the process may move to block 160, where this memory buffer can be frozen at any point by a user for review and be displayed on a display screen 20 (e.g., a display screen of the mobile device). Alternatively, the process may move to block 140, where the user may choose to save a capture, in which the mobile device automatically writes the appropriate images from the memory buffer into a local or cloud database 40 for storage.

Figure 2A:
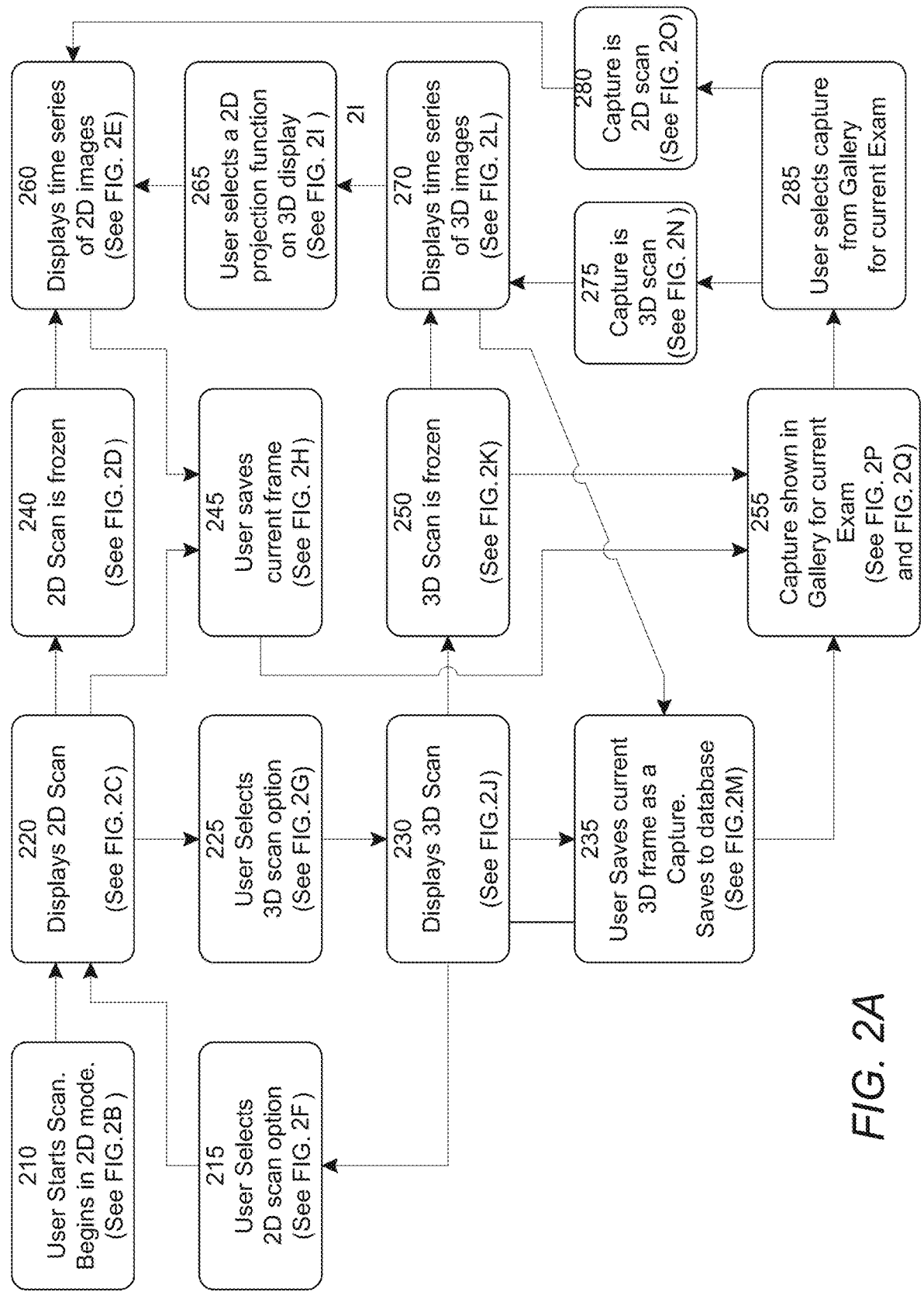
FIG. 2A illustrates an exemplary user workflow for scanning and visualizing ultrasound images.

FIG. 2A illustrates an exemplary user workflow for transitioning from scanning to displaying saved ultrasound images. The workflow states a user can be in include: scanning, frozen and review. "Scanning" shows images directly from the scanner 10. "Frozen" shows the last N seconds of images from the scanner 10. "Review" shows images that are explicitly saved. During a workflow, cineloops can be saved while scanning or while frozen. 2D and 3D images can be saved from any cineloop. A cineloop can be converted into a 3D image. In addition, all saved captures can be automatically displayed as thumbnails in a gallery. Selecting any thumbnail automatically displays the corresponding capture for review. A user can return to scanning at any time. In response to the user input or selection of certain transition between states, modifications is automatically made to the underlying image data by the disclosed system. The disclosed unified user interface may show the user relevant functions for transitioning between workflow states or display variants, based on the current state in the workflow.

Figure 2B:
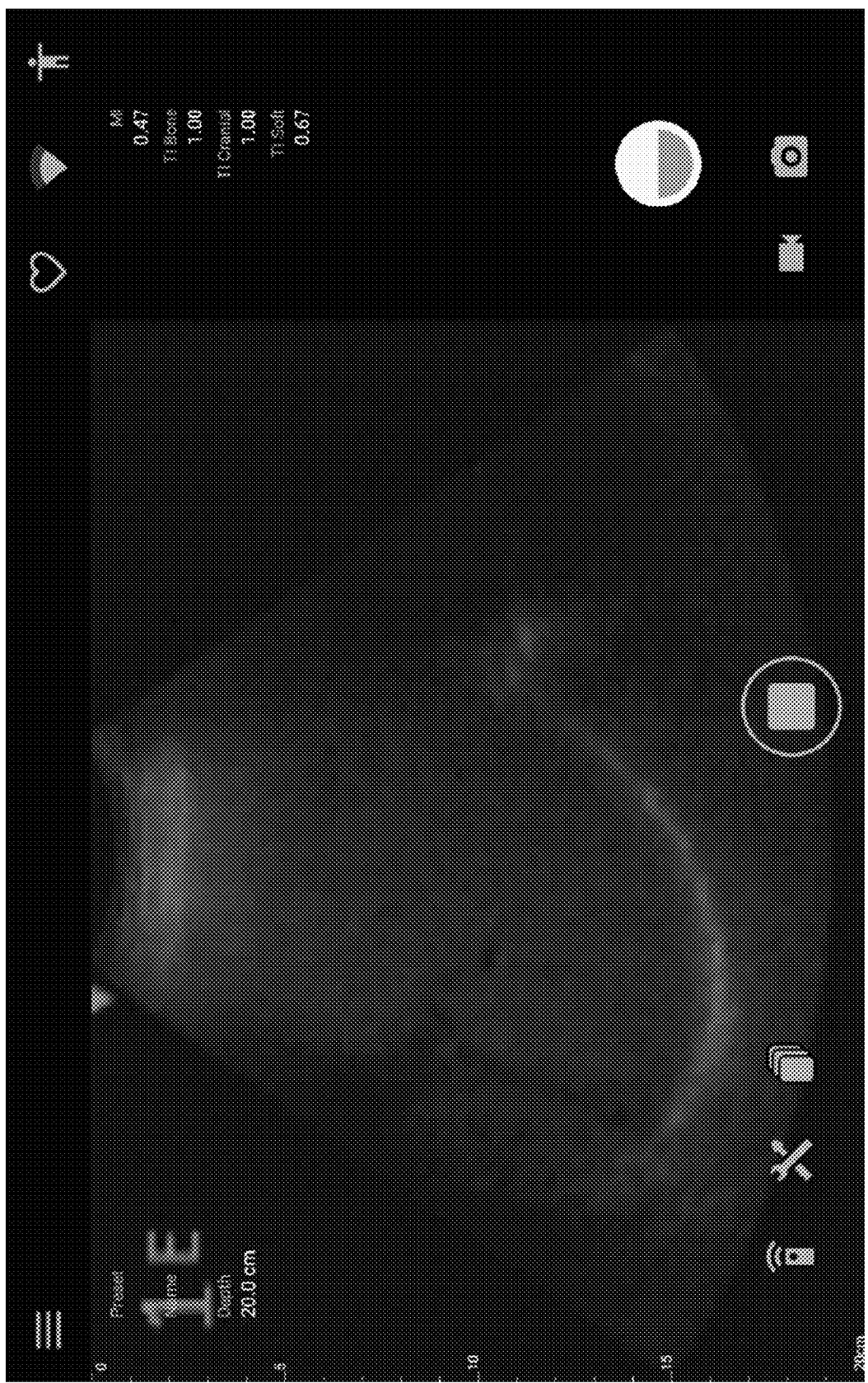
FIGS. 2B-2Q show how an embodiment of a unified user interface appears at each block of the exemplary user workflow.
Figure 2C:
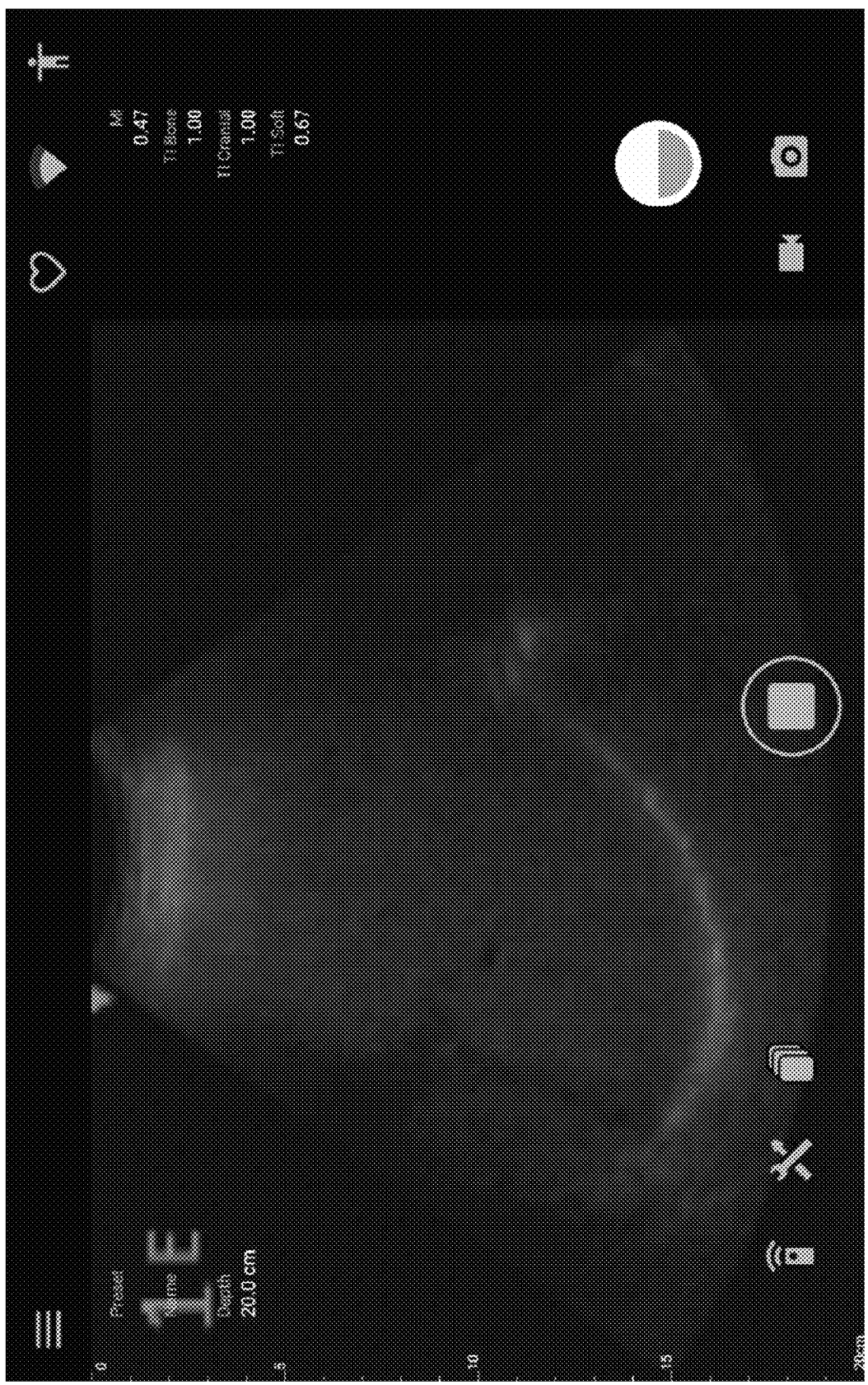
Figure 2D:
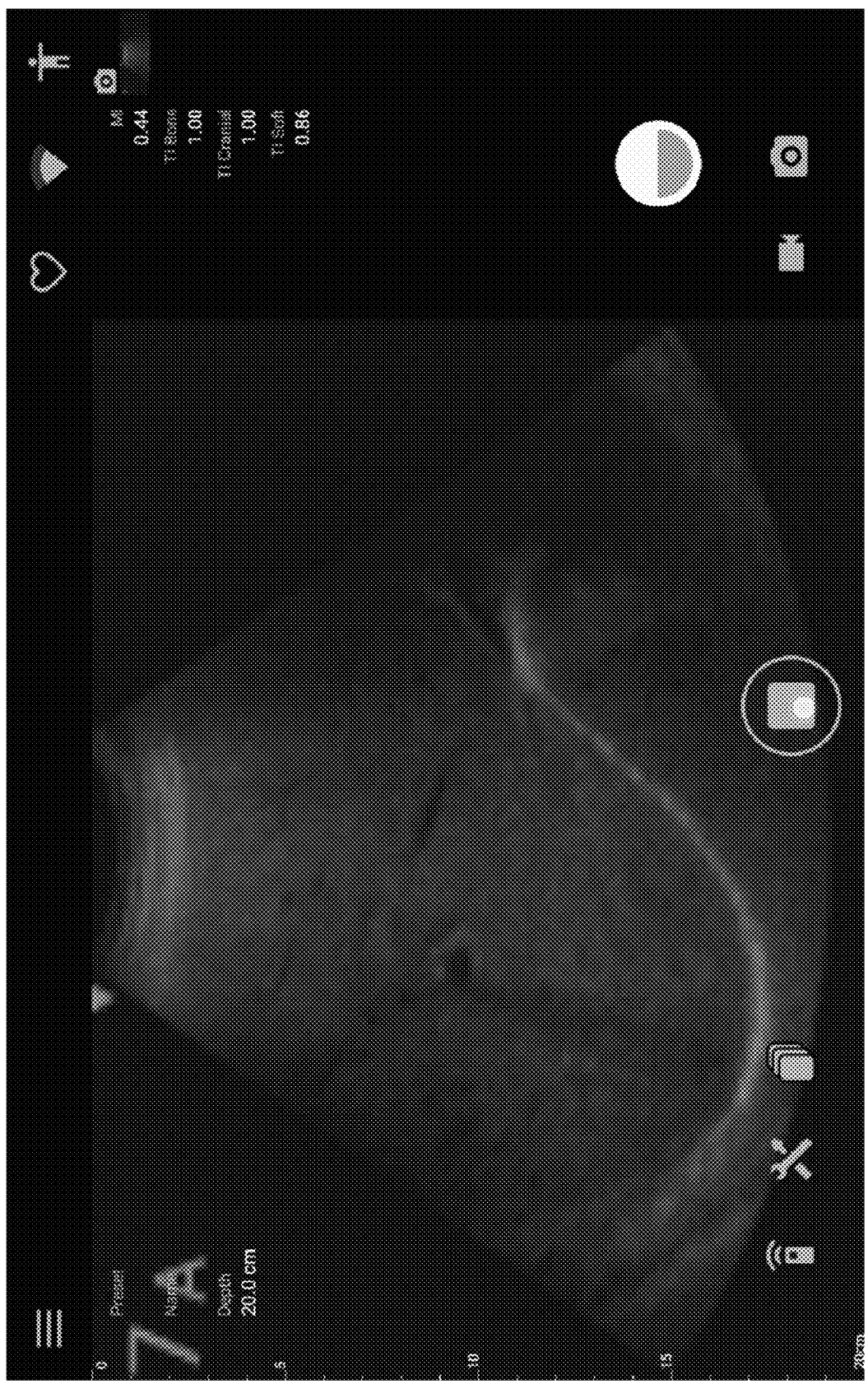
Figure 2E:
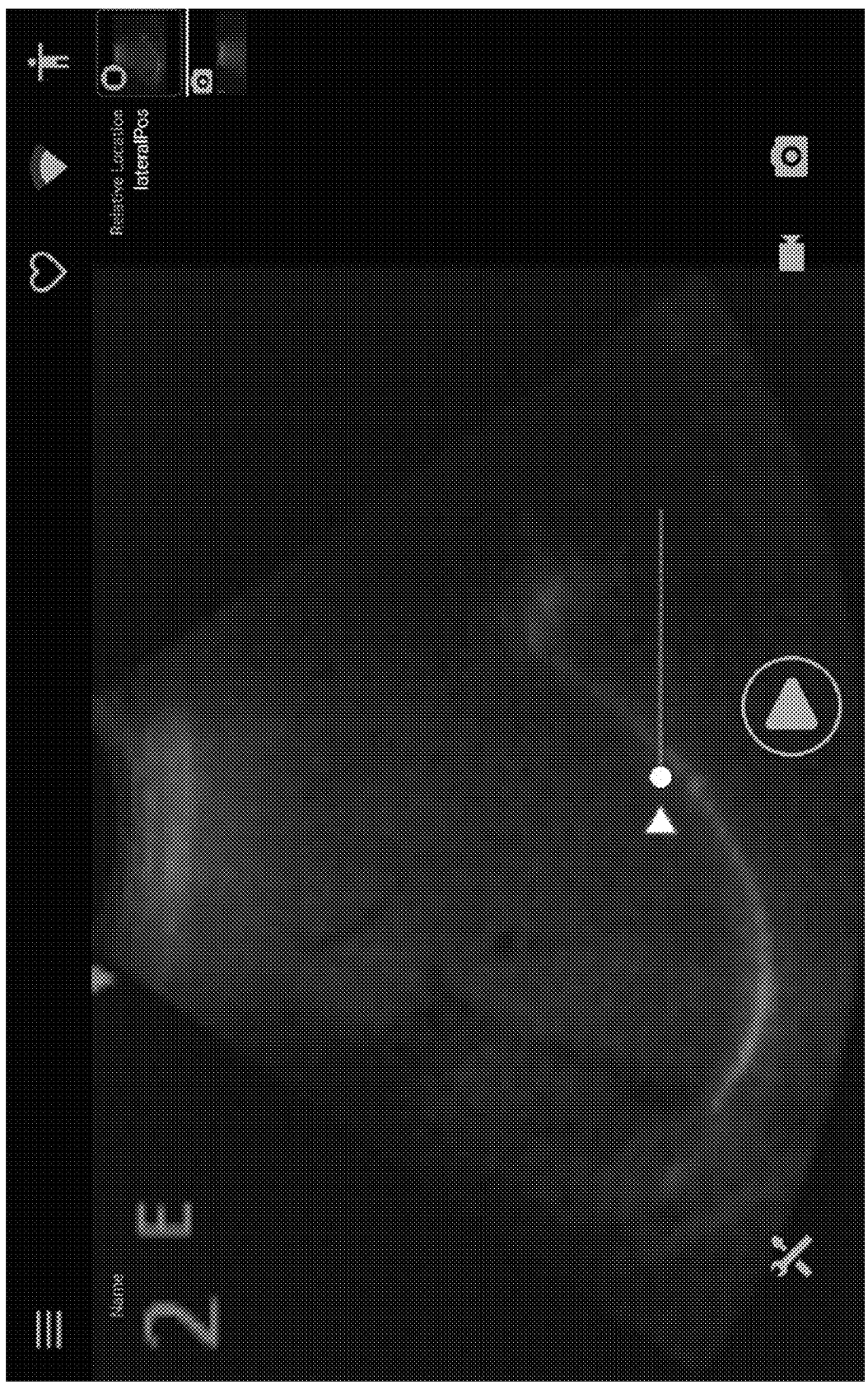
Figure 2F:
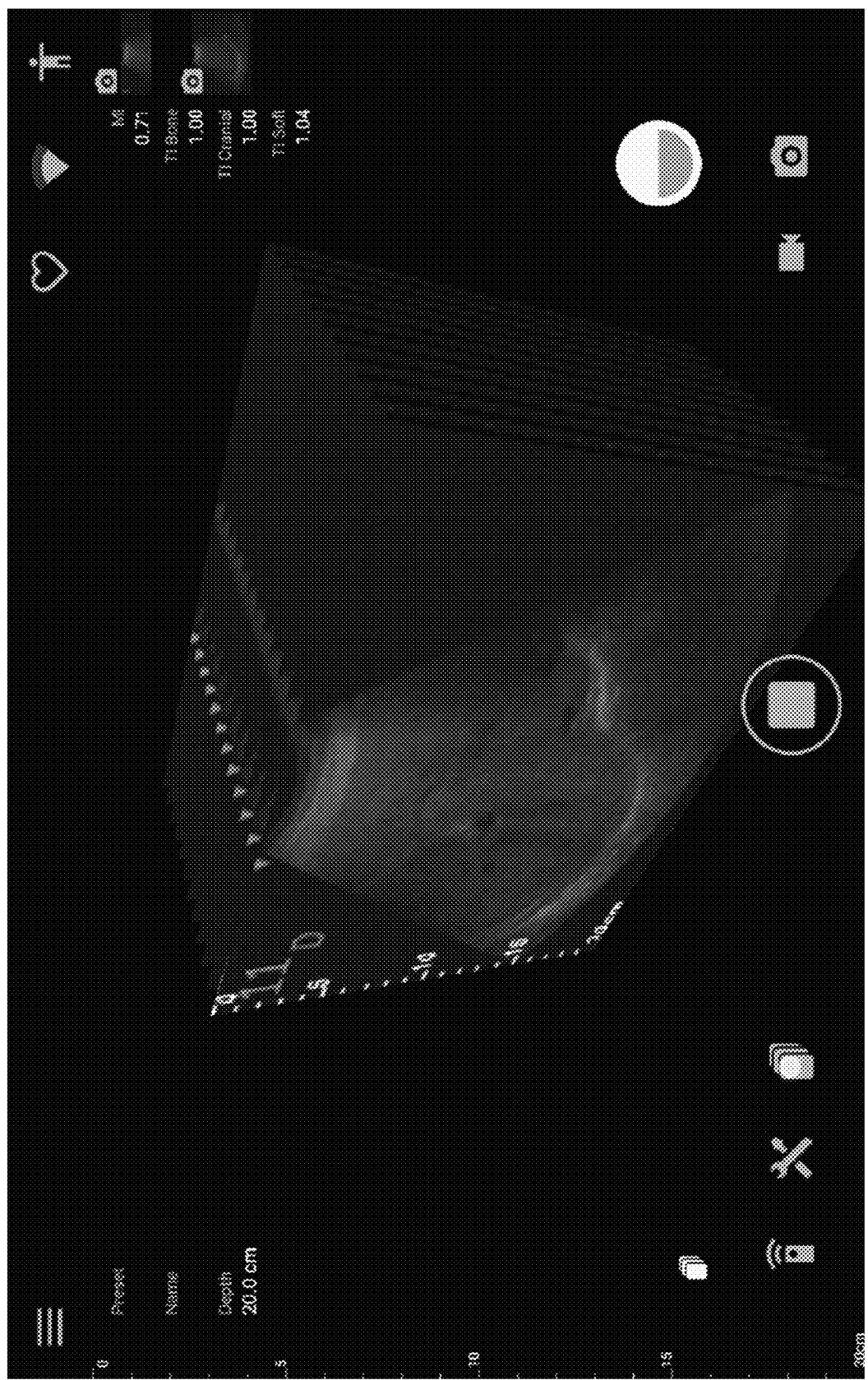
Figure 2G:
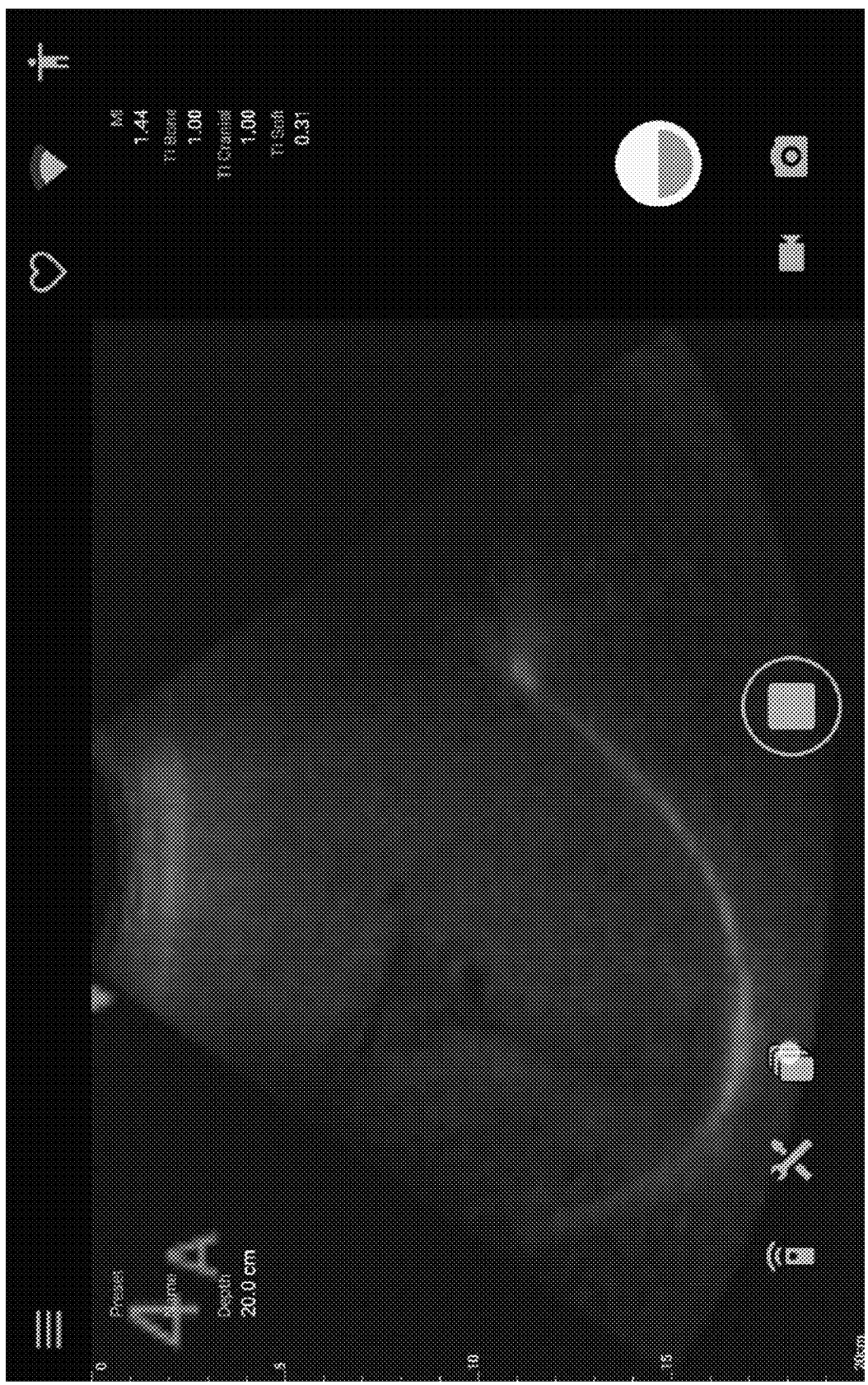
Figure 2H:
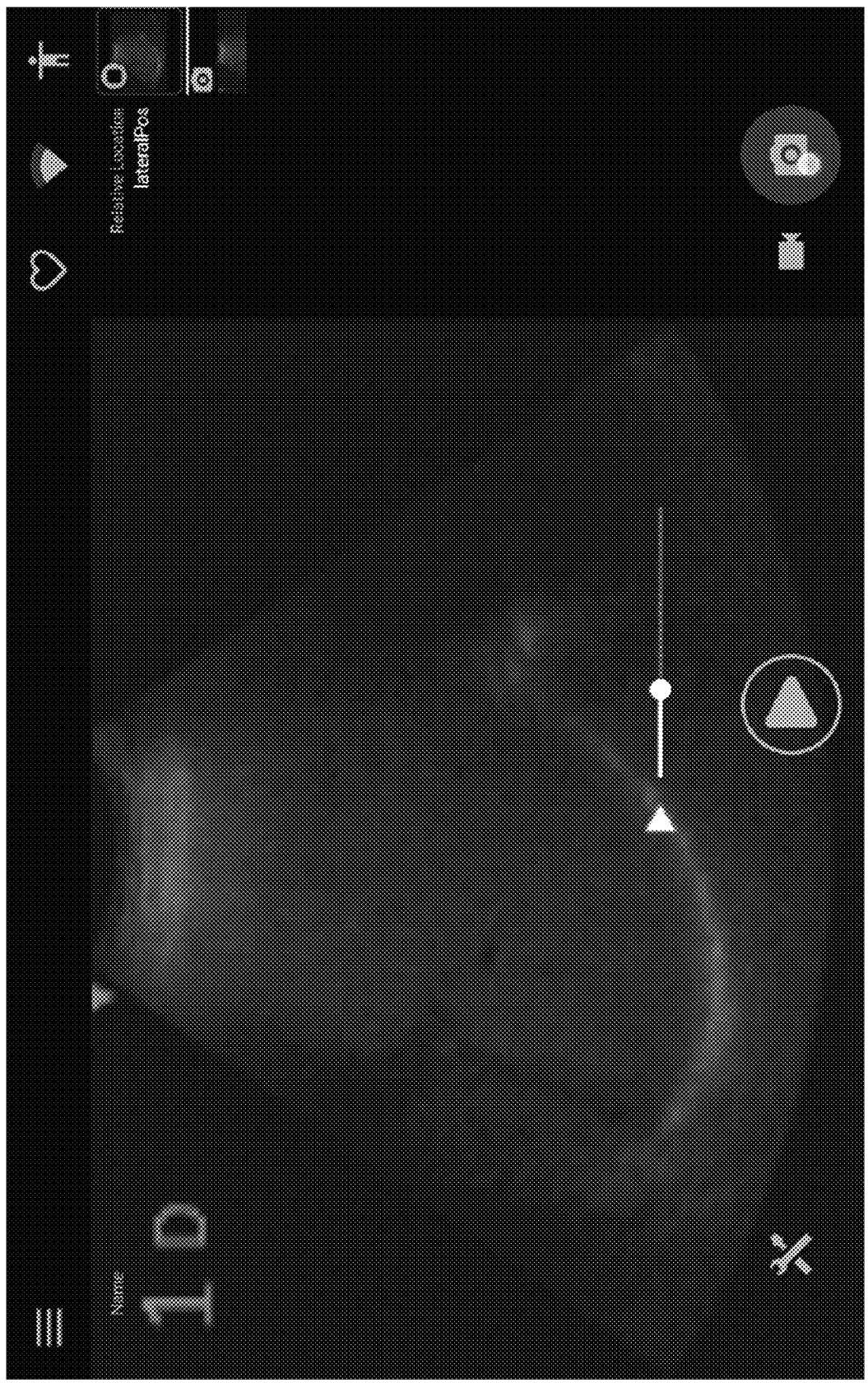

In the exemplary user workflow shown in FIG. 2A, the workflow may start at block 210, where the system may automatically begin in the 2D scan mode by default after the user starts a scan, and the ultrasound device 10 begins to acquire 2D ultrasound images. FIG. 2B shows how an embodiment of a unified user interface appears at block 210. Alternatively, the workflow may start at block 215, where the user manually selects the 2D scan option, and the ultrasound device 10 begins to acquire 2D ultrasound images. FIG. 2F shows how an embodiment of a unified user interface appears at block 215. When the ultrasound device 10 is acquiring 2D ultrasound images, the workflow may move to block 220, where the system automatically displays the 2D scan to the user. FIG. 2C shows how an embodiment of a unified user interface appears at block 220. While viewing the 2D scan, the user may choose to move the workflow to block 225, where the user manually selects the 3D scan option; to block 240, where the 2D scan is frozen; or to block 245, where the user saves the current frame, via relevant functions shown to the user by the unified user interface. FIG. 2D shows how an embodiment of a unified user interface appears at block 240. FIG. 2G shows how an embodiment of a unified user interface appears at block 225. FIG. 2H shows how an embodiment of a unified user interface appears at block 245.

Figure 2I:
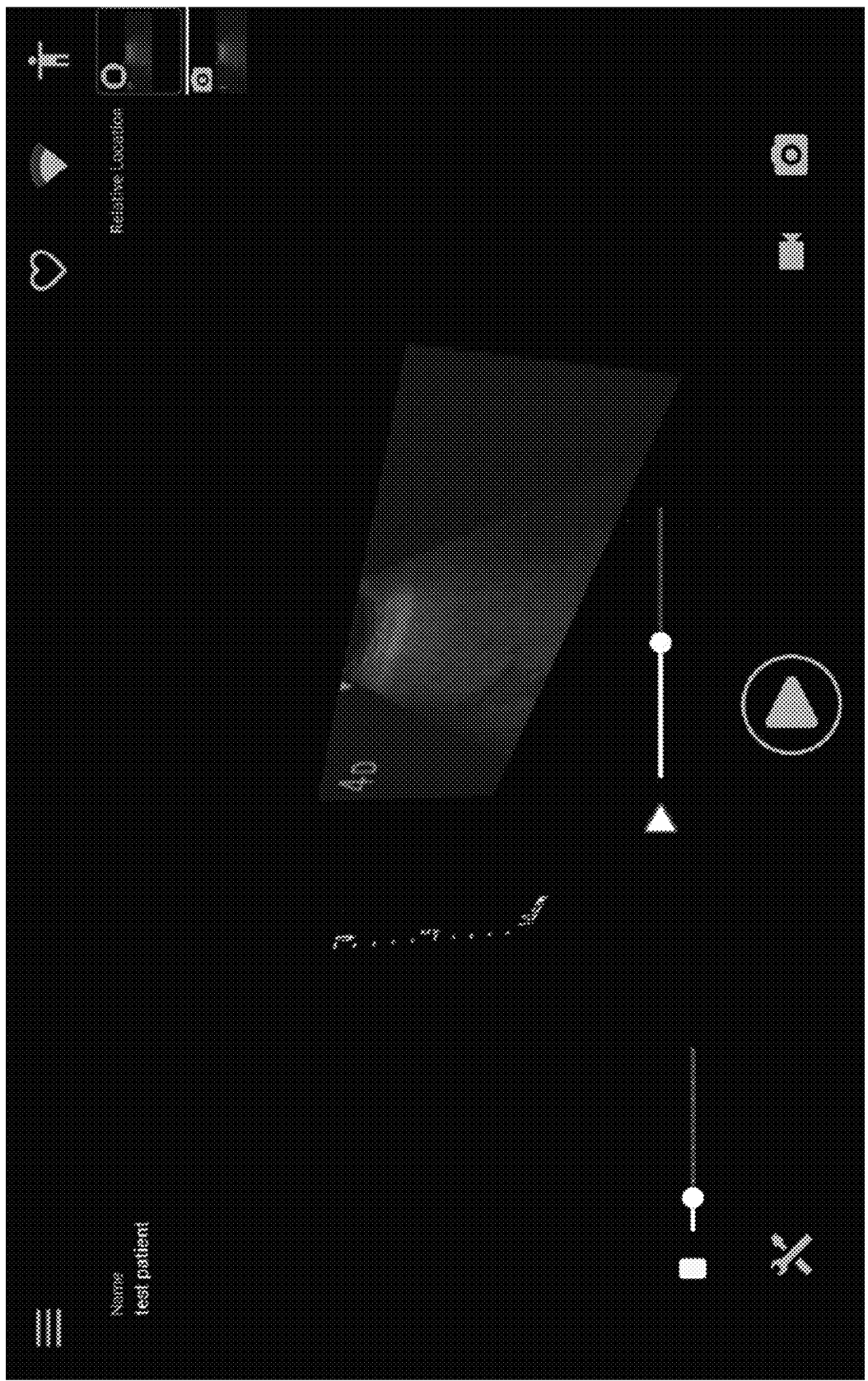
Figure 2J:
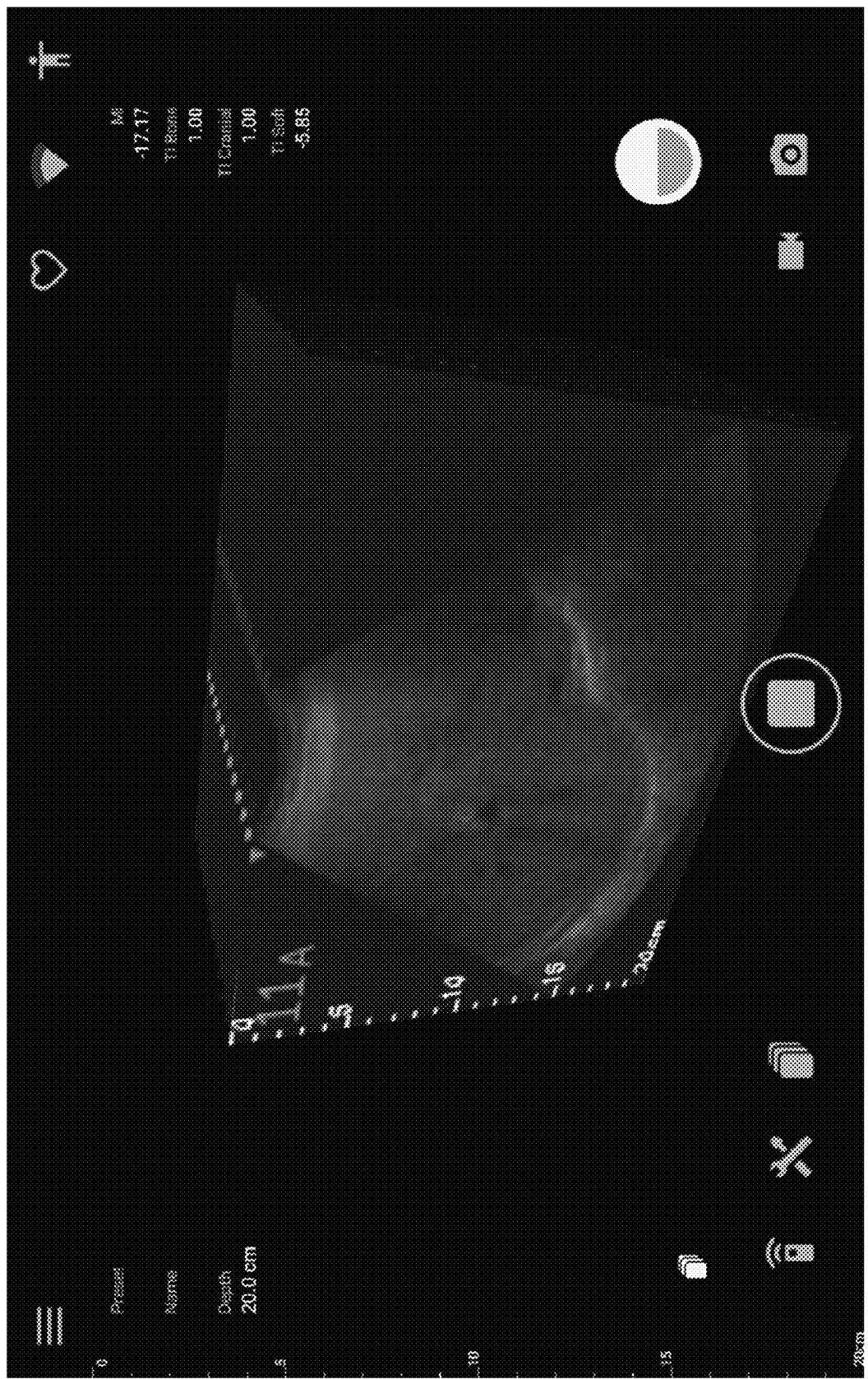
Figure 2K:
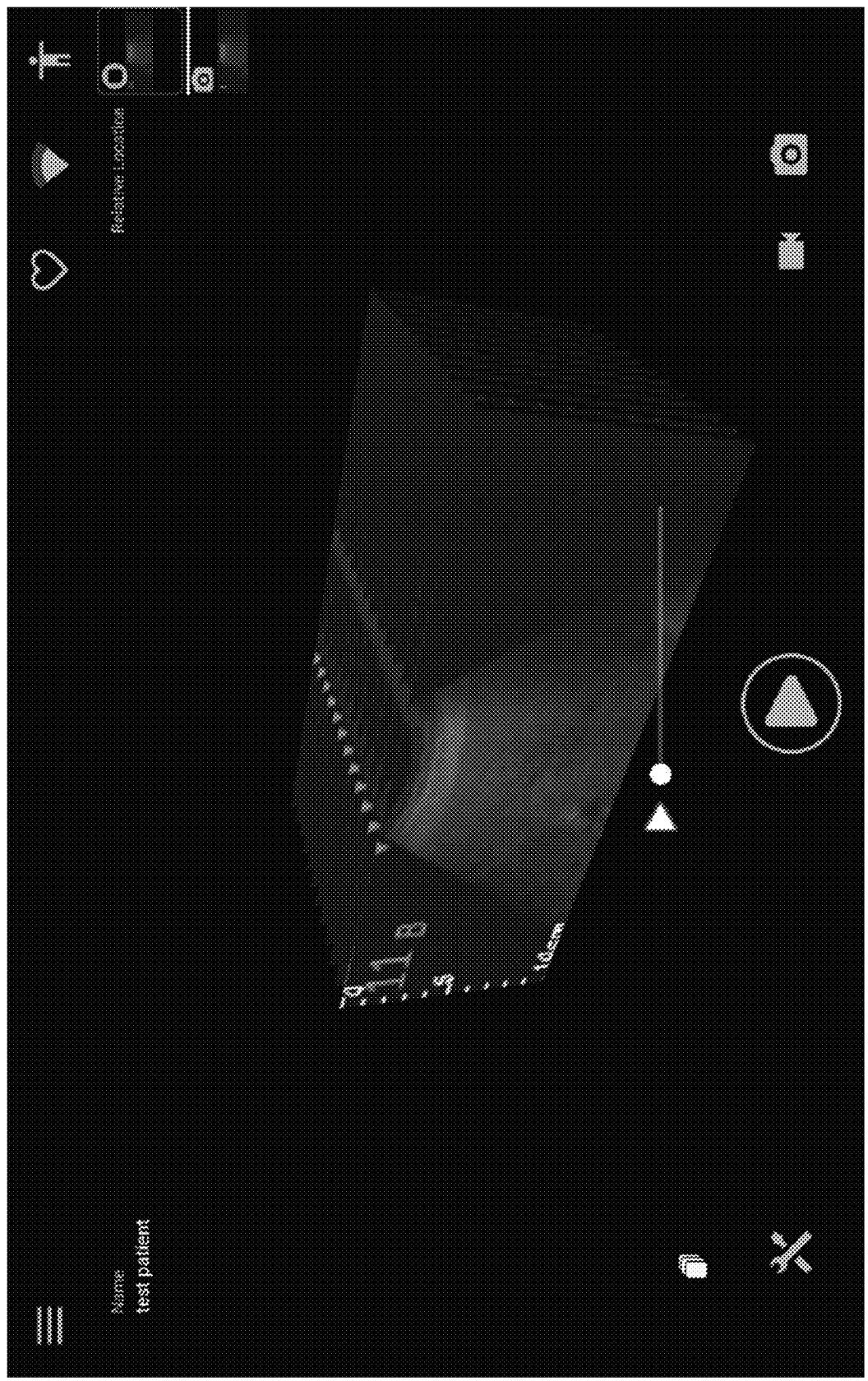
Figure 2L:
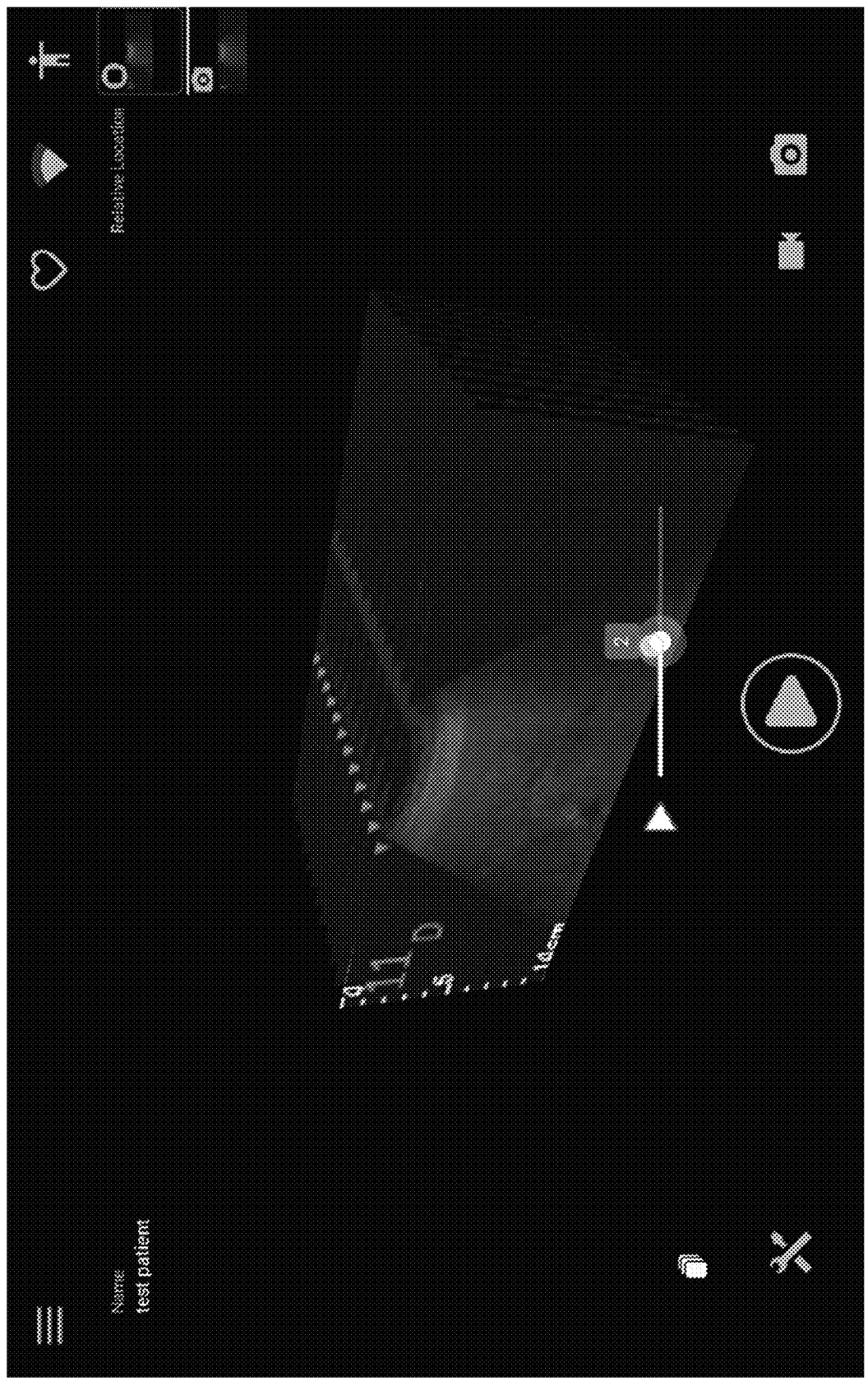
Figure 2M:
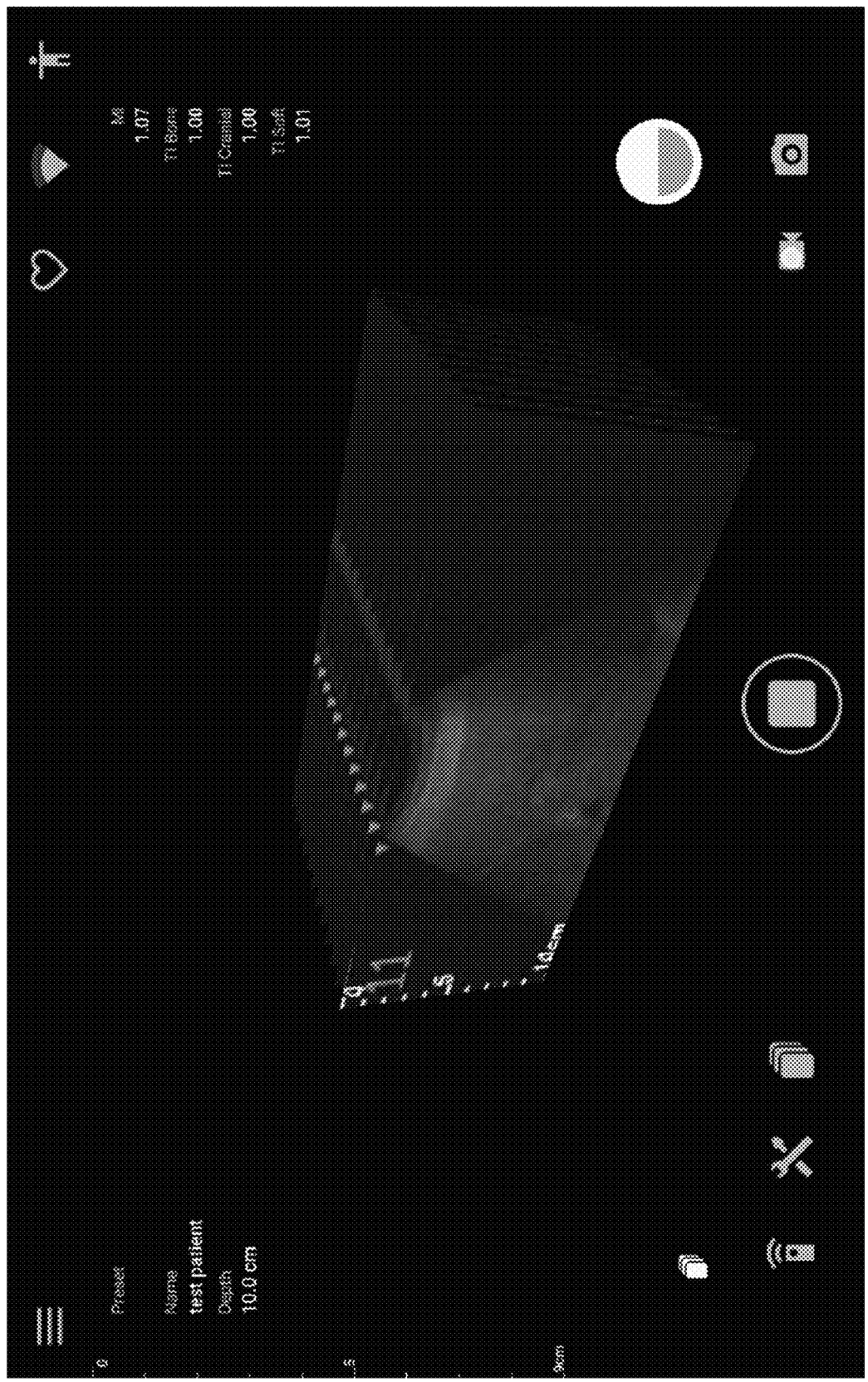
Figure 2N:
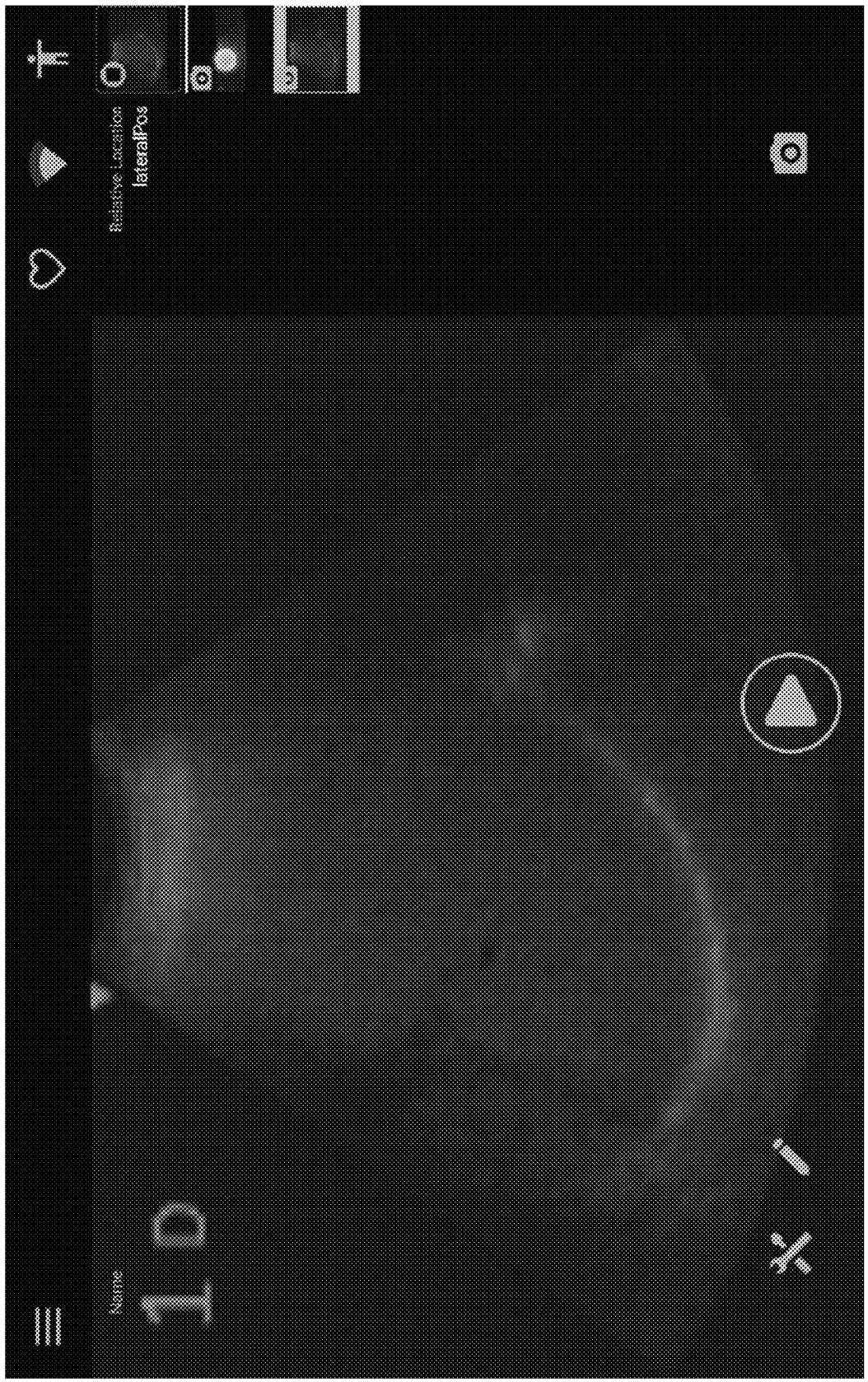
Figure 20:
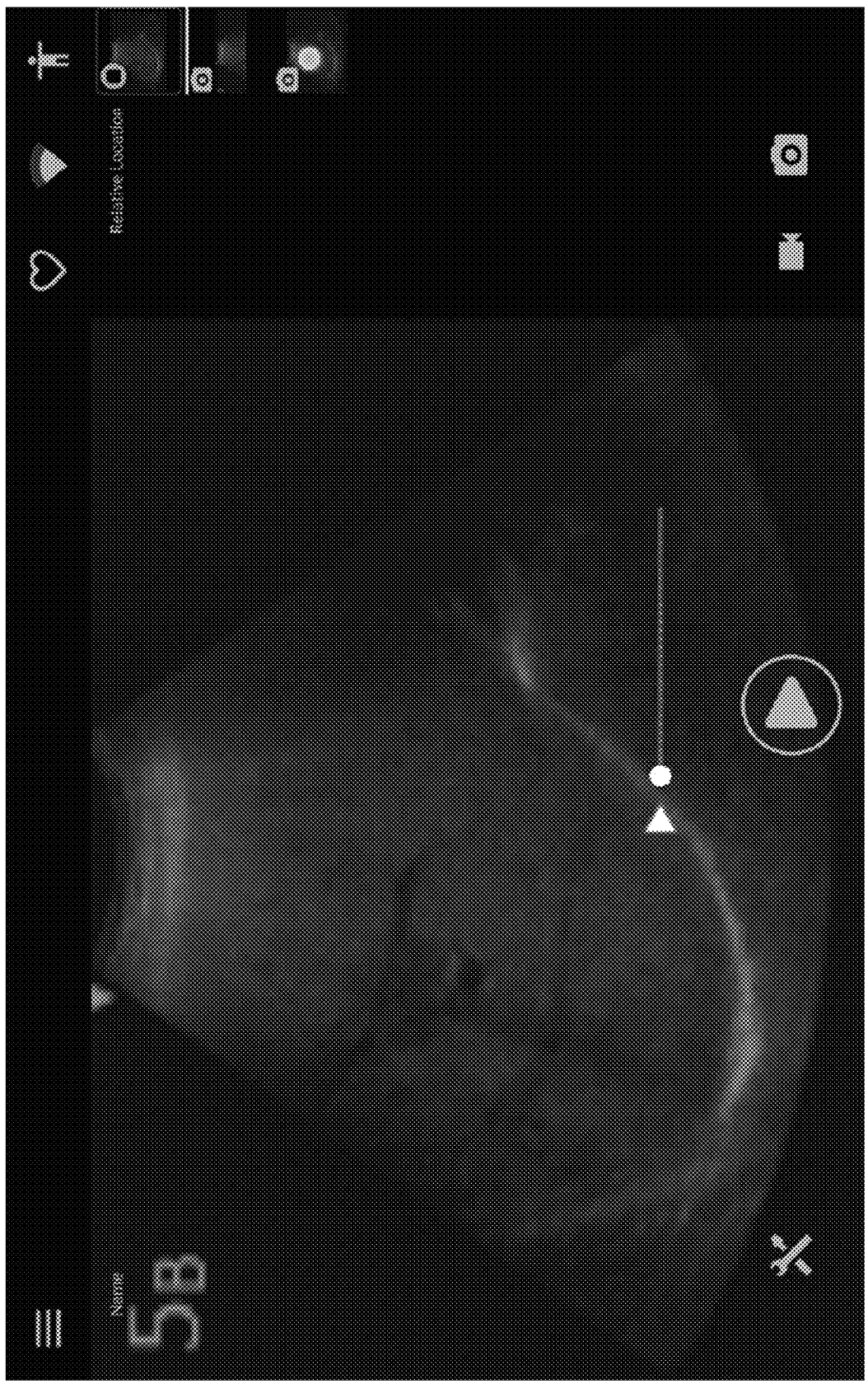
Figure 2P:
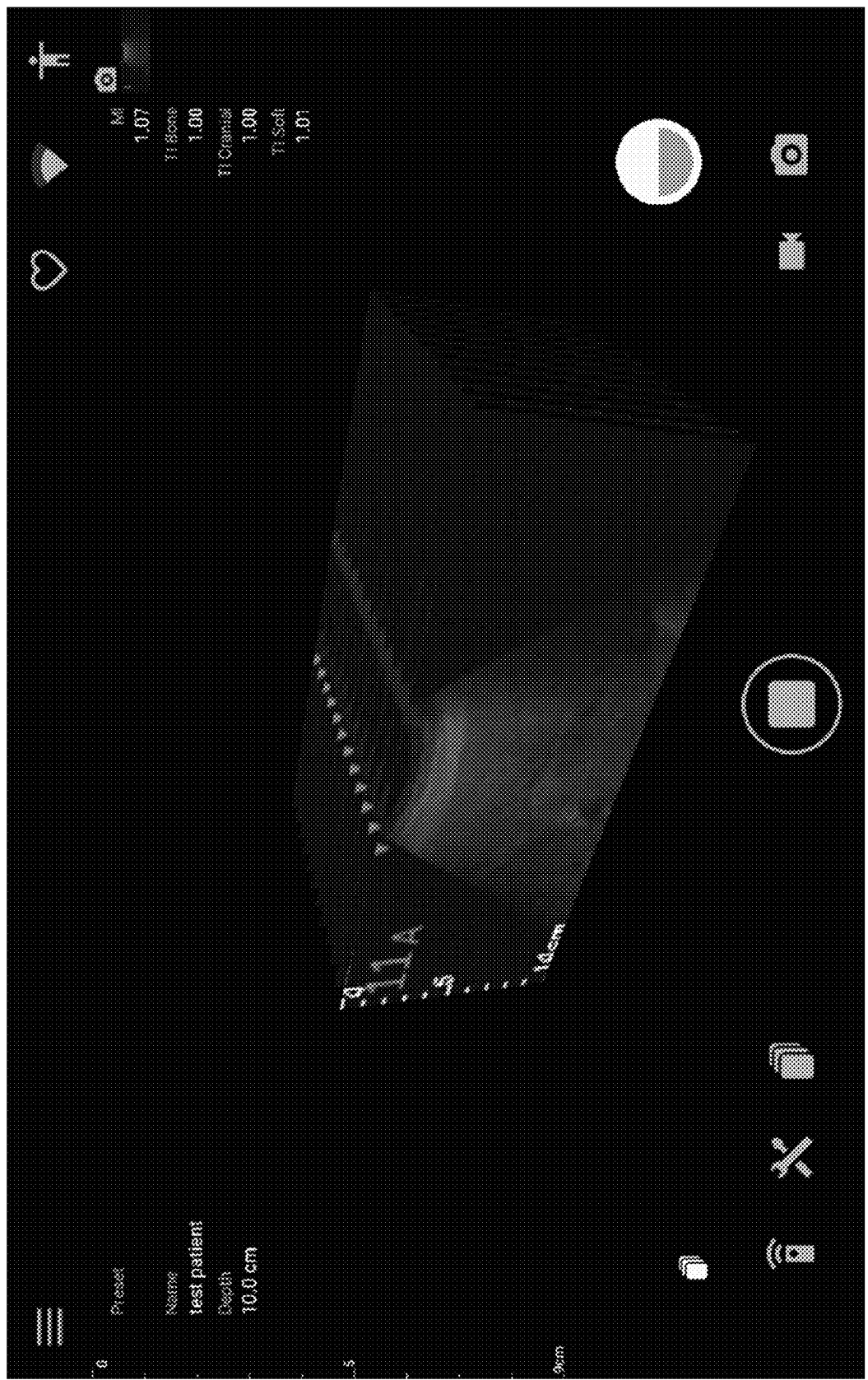
Figure 2Q:
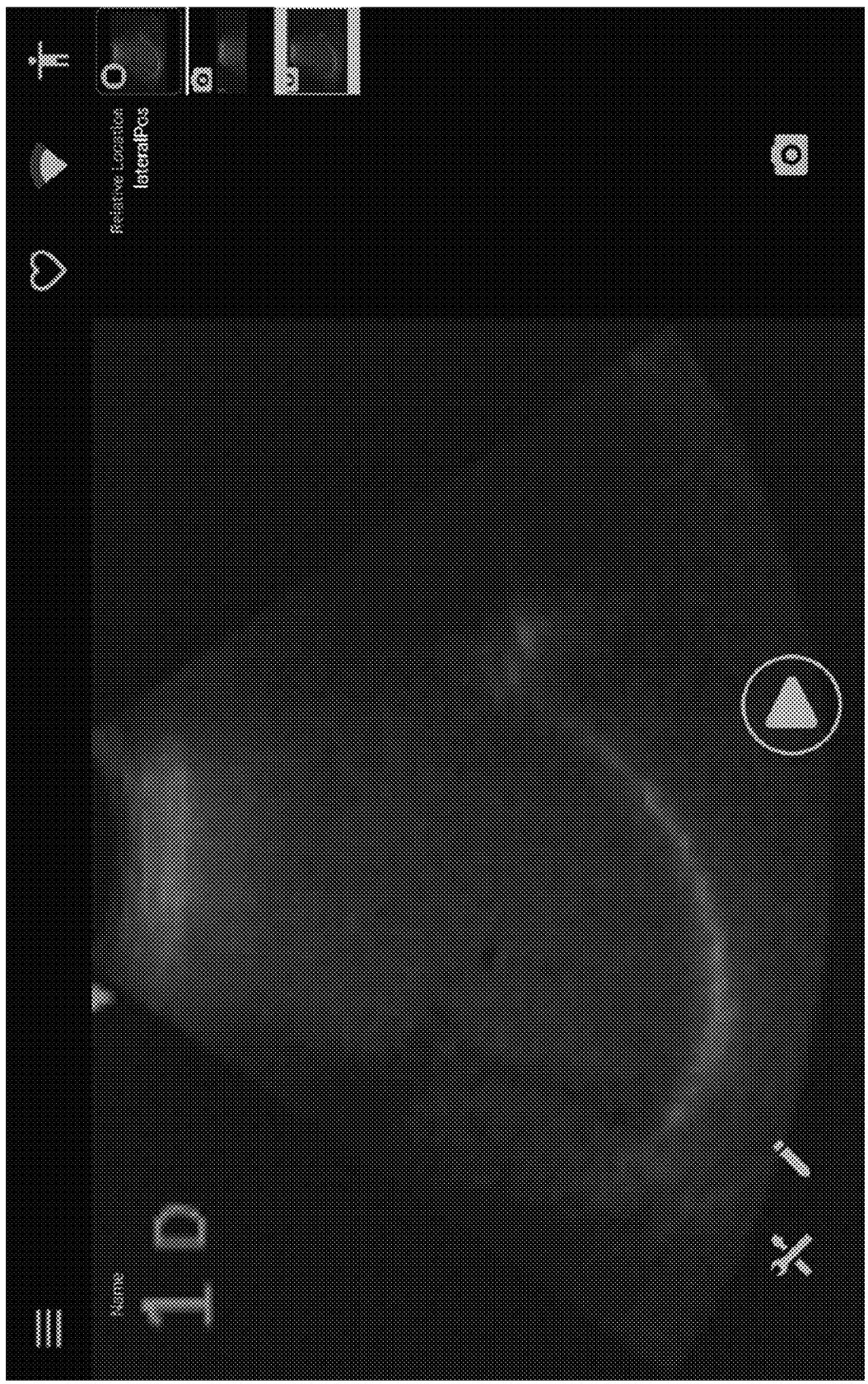

At block 225, after the user selects the 3D scan option and the ultrasound device 10 begins to acquire 3D ultrasound images, the workflow may move to block 230, where the system automatically displays the 3D scan to the user. FIG. 2J shows how an embodiment of a unified user interface appears at block 230. While viewing the 3D scan, the user may choose to move the workflow to block 235, where the user choose to save the current 3D frame as a capture and the system automatically saves the capture to a database 40; to block 250, where the 3D scan is frozen; or back to block 215, where the user choose to go back to 2D scan mode. FIG. 2M shows how an embodiment of a unified user interface appears at block 235. At block 235, after the system saves the capture to the database 40, the workflow may move to block 255, where the capture is automatically shown in a gallery for the current exam. FIG. 2K shows how an embodiment of a unified user interface appears at block 250. FIGS. 2P and 2Q show how an embodiment of a unified user interface appear at block 255.

At block 240, after the 2D scan is frozen, the workflow may move to block 260, where the system automatically displays time series of the last N seconds of 2D images from the scanner 10. FIG. 2E shows how an embodiment of a unified user interface appears at block 260. While the system is displaying time series of the 2D images, the workflow may move to block 245, where the user saves the current frame. At block 245, after the user saves the current frame, the workflow may move to block 255, where the capture is automatically shown in the gallery for the current exam.

At block 250, after the 3D scan is frozen, the system may move to block 270, where the system automatically displays time series of the last N seconds of 3D images from the scanner 10. FIG. 2L shows how an embodiment of a unified user interface appears at block 270. While the system is displaying time series of the 3D images, the workflow may move to block 265, where the user selects a function for a certain 2D projection of the 3D images and the system automatically performs the 2D projection, taken into account the relative spatial position and orientation of each individual image given by the IMU value of the scanner 10. FIG. 2I shows how an embodiment of a unified user interface appears at block 265. At block 265, after the 2D projection is performed, the system may move to block 260, where the system automatically displays time series of the last N seconds of 2D images from the scanner 10.

At block 255, while capture is shown in the gallery for the current exam, the workflow may move to block 285, where the user selects a capture from the gallery for the current exam. At block 285, after the user selects a capture, the workflow may move to block 280 if the selected capture is a 2D scan; or to block 275 if the selected capture is a 3D scan. FIG. 2N shows how an embodiment of a unified user interface appears at block 275. FIG. 2O shows how an embodiment of a unified user interface appears at block 280. At block 280, if the selected capture is determined by the system to be a 2D scan, the workflow may move to block 260, where the system automatically displays time series of the last N seconds of 2D images from the scanner 10. At block 275, if the selected capture is determined by the system to be a 3D scan, the workflow may move to block 270, where the system automatically displays time series of the last N seconds of 3D images from the scanner 10.

At block 270, while the system displays time series of 3D images, the workflow may move to block 235, where the user choose to save the current 3D frame as a capture and the system automatically saves the capture to the database 40; or to block 265, where the user selects a function for a certain 2D projection of the 3D images and the system automatically performs the 2D projection.

Figure 3:
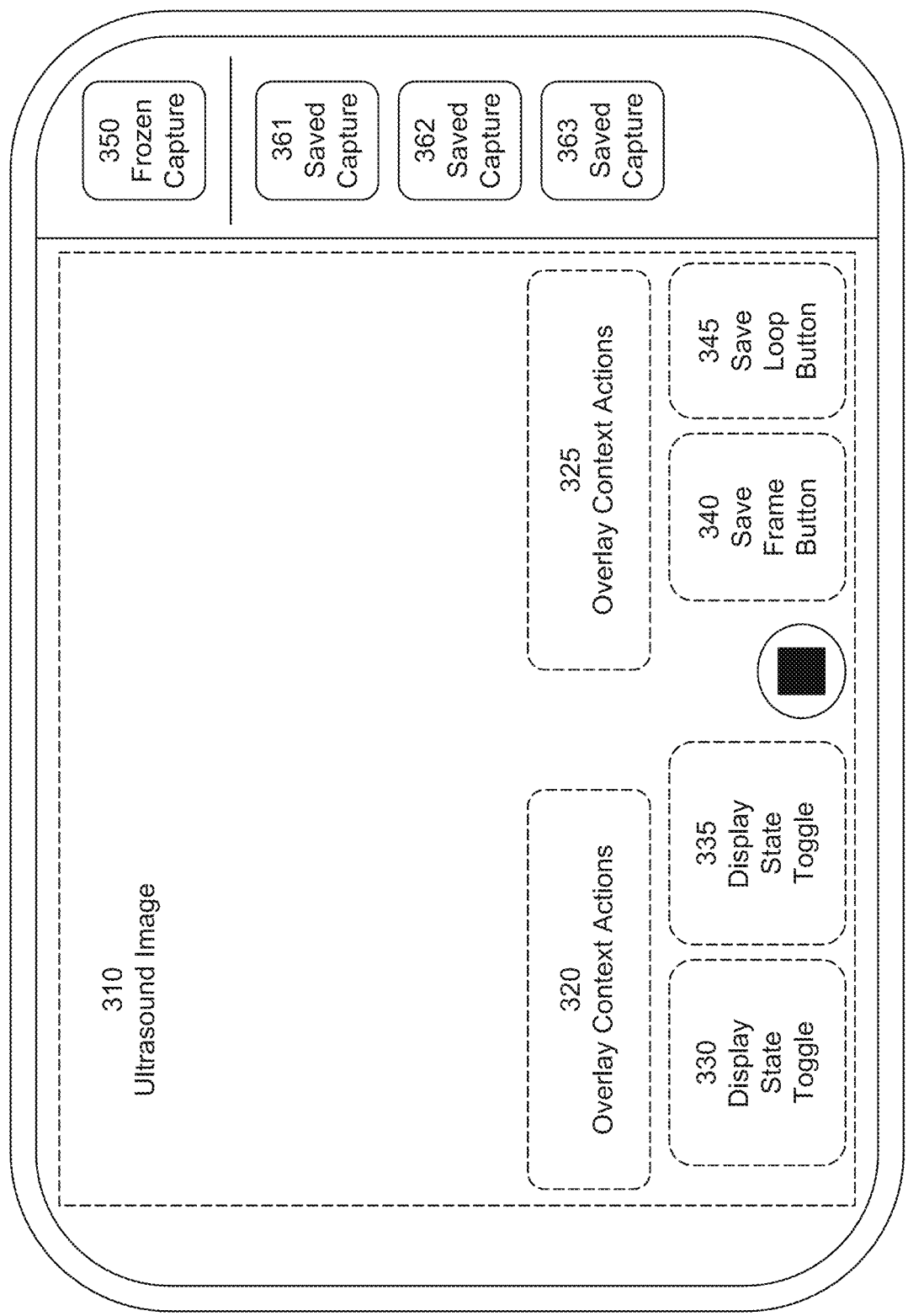
FIG. 3 is an embodiment of a unified user interface.

FIG. 3 is an embodiment of a unified user interface layout, having functions or actions which enables the usage workflow and the transitions described in connection with FIG. 2. In the unified user interface, the positions of the various elements are flexible and can be arranged on the screen for different device orientations and screen resolutions. For example, in FIG. 3, the saved images panel gallery (saved captures 361, 362, and 363) may run along the side. In alternative embodiment, the saved images panel gallery (saved captures 361, 362, and 363) may run along the bottom edge when the device is in portrait mode. Additionally, large mobile devices like tablets may show more actions as single click interface elements, while on smaller screens such as lower-resolution phones, will instead be elements requiring two or more touch events to display. The contextual user interface may be configured to react to the display environment in addition to the underlying data to display, in order to show all available options and scan data within a single screen.

In the embodiment of a unified user interface shown in FIG. 3, from the same screen a user can start or stop scanning using the home button; select saved captures 361, 362, and 363 for the current exam; and select the frozen capture 350. At any point in the process, the user can save the current ultrasound image 310 (which may be a frame, projection, or time-series loop) using the save frame button 340 or the save loop button 345. If it is not possible to take one of these actions, the relevant button will be hidden from the user (e.g., a video of a single frame cannot be saved). When viewing 2D or 3D cineloops, the user can replay the cineloop or manually scroll through the cineloop. When running the loop, the user can adjust the replay speed. When displaying 3D images and cineloops, the slices can be viewed all at once or riffled one at a time either automatically or manually.

Moreover, for any capture that is being displayed, whether from saved scans or an active scan, display state actions can be taken, such as switching between 2D and 3D using the display state toggles 330 and 335. Once selected, the appropriate controls will be shown as contextual actions (context actions, i.e., controls that appear only for the appropriate context), and such context actions, e.g., 320 and 325, will be overlaid on the screen. For example, a frame selector will be shown if a loop is displayed. The frame selector may be applicable to time series data, but not individual frames. For another example, a slice selector will be shown if a 3D image is displayed. The slice selector may be used for choosing between showing entire 3D image or a single "slice", or for riffling between the slices. The actions associated with both saving and displaying may transform the underlying image and the captured data. The system may automatically determine the state of the underlying image and capture data, and use such information to automatically determine the available transformations that can be done to the data as well as how the data should be displayed.

Figure 4B:
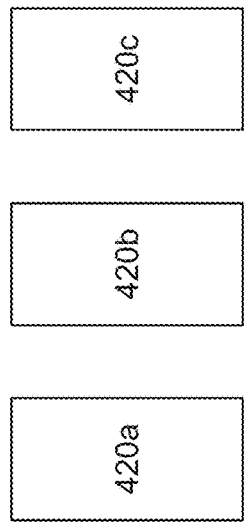
FIG. 4B shows example slices of the object from different positions.
Figure 4C:
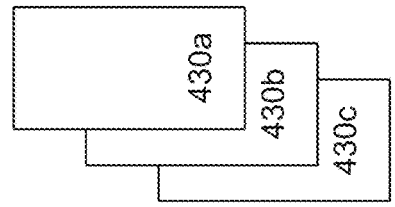
FIG. 4C illustrates an example of stacking slices to form a 3D image.
Figure 4A:
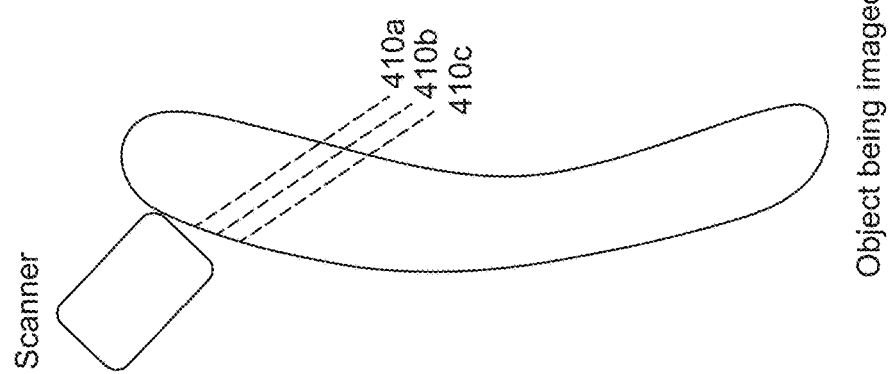
FIG. 4A shows an example of imaging an object with an ultrasound scanner.

FIGS. 4A-4C demonstrate what is meant by a "slice" when specified in an image. FIG. 4A shows an example of imaging an object with an ultrasound scanner 10. The object is being imaged at different scan positions 410a, 410b, and 410c. FIG. 4B shows example slices 420a, 420b, and 420c of the object from the different scan positions 410a, 410b, and 410c, respectively. Each slice includes a plurality of scanned image(s) from a spatial range near the scan position. For example, the slice 420a includes a plurality of scanned image(s) from a spatial range near the scan position 410a. In some embodiment, the plurality of scanned image(s) from a spatial range can be shown as a time series of 2D images, where the plurality of scanned image(s) constituting a slice is shown over time. In other embodiments, since each of the image data constituting a slice has a known relative scanner position with respect to each other, the image data constituting a slice can be rendered in 3D. FIG. 4C illustrates an example of stacking a plurality of slices 430a, 430b, and 430c to form a 3D image.

Figure 5C:
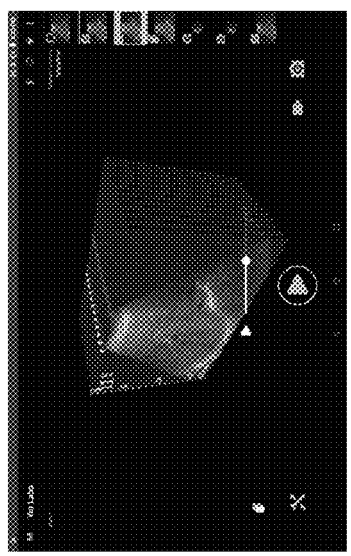
FIG. 5C shows an example of a 4D capture.
Figure 5B:
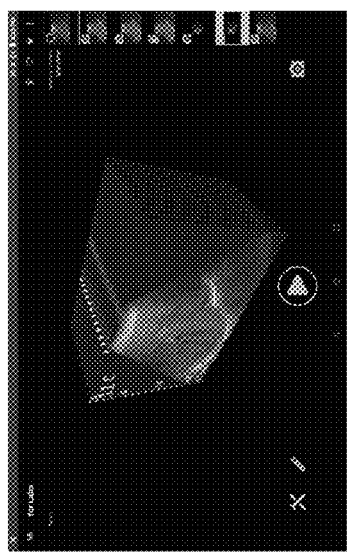
FIG. 5B shows an example of a 3D capture.
Figure 5A:
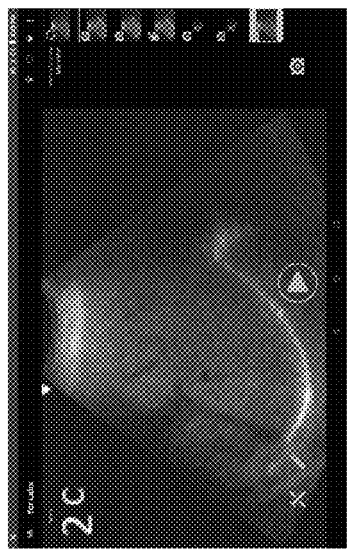
FIG. 5A shows an example of a 2D capture.

In a user workflow, any reference to display may render the capture or scanning stream to the image part of the layout. The functional areas may then show the various context-based actions (e.g., saving a single frame). The screenshots in FIGS. 5A-5C show how the different renderings and available actions differ for different capture types. Further, FIGS. 5A-5C show how all saved captures are displayed along the edge in the gallery view, and selecting any capture will make it the forefront/displayed capture. FIG. 5A shows an example screenshot of a 2D capture, and within the same viewer, a gallery selector on the right. FIG. 5B shows an example screenshot of a 3D capture, and within the same viewer, a gallery selector on the right. FIG. 5C shows an example screenshot of a 4D capture, and within the same viewer, a gallery selector on the right. FIGS. 5A-5C also show conversion actions (e.g., taking 2D image from a 3D capture) or selecting different modes when applicable based on the foreground capture. In some embodiments, the available actions that can be performed on each of the images include saving and transforming between display variants. In some embodiments, the available functions further include that 2D captures can be zoomed, rotated, or moved. In some embodiments, the available functions further include that 3D captures can be zoomed, rotated, tilted, or moved. In some embodiments, the available functions further include that 3D rotation and tilting of the captures can be achieved by using the touch screen. Alternatively, 3D rotation and tilting of the captures can be achieved by physically orienting or moving the tablet or mobile phone, based on the tablet or mobile phone's IMU values.

Example Method of Visualizing and Labeling Ultrasound Images

Figure 6:
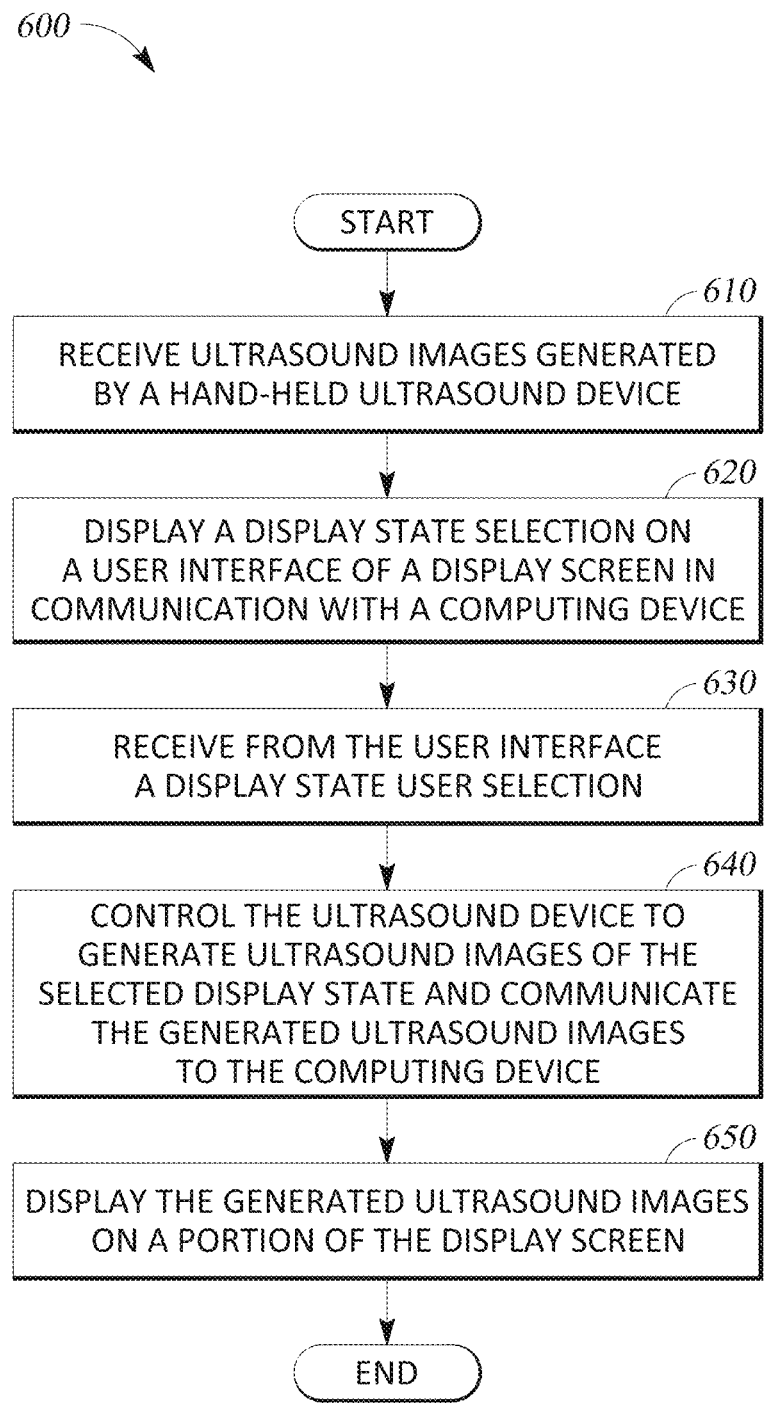
FIG. 6 is a process flow diagram illustrating an example method for visualizing ultrasound images generated by a hand-held ultrasound device.

FIG. 6 illustrates an example flowchart depicting a method 600 for visualizing two-dimensional (2D), three-dimensional (3D), and four-dimensional (4D) ultrasound images generated by a hand-held ultrasound device 10, in accordance with embodiments described above. Although the method 600 is illustrated in a particular order, the steps may be performed in a different order, or omitted, altered, additional steps can be added or any combination of these are possible. Other process flows are possible.

The method 600 moves from a start state to block 610 of receiving ultrasound images generated by a hand-held ultrasound device 10. The method 600 then moves to block 620 of displaying a display state selection on a user interface of a display screen 20 in communication with a computing device 30, where the display state selection may be indicating to receive 2D or 3D images. The method 600 then moves to block 630 of receiving from the user interface a display state user selection indicating to generate 2D or 3D images. The method 600 then continues to block 640 and the ultrasound device 10 is controlled to generate ultrasound images of the selected display state and communicate the generated ultrasound images to the computing device 30, in response to receiving the display state user selection. The method 600 then moves to block 650, displaying the generated ultrasound images on a portion of the display screen 20.

In some implementations, generating ultrasound images may include generating 2D images. In some implementations, the method 600 further includes displaying a capture graphical indicator on the user interface, for capturing one of the 2D images displayed on the display screen 20; and in response to receiving user input selecting the capture graphical indicator, storing currently displayed 2D image.

In some implementations, generating ultrasound images may include generating 3D images. In some implementations, the method 600 further include displaying a capture graphical indicator on the user interface, for capturing one of the 3D images displayed on the display screen 20; and in response to receiving user input selecting the capture graphical indicator, storing currently displayed 3D image.

In some implementations, generating ultrasound images may include generating 2D images. In some implementations, the method 600 further includes displaying a 2D frozen review graphical indicator on the user interface, for reviewing a most recent portion of the 2D images generated by a hand-held ultrasound device 10; and in response to receiving user input selecting the 2D frozen review graphical indicator, displaying the most recent portion of the 2D images on a portion of the display screen 20.

In some implementations, the method 600 further includes displaying time series of 2D images on a portion of the display screen 20.

In some implementations, generating ultrasound images may include generating 3D images. In some implementations, the method 600 further includes displaying a 3D frozen review graphical indicator on the user interface, for reviewing a most recent portion of the 3D images generated by a hand-held ultrasound device 10; and in response to receiving user input selecting the 3D frozen review graphical indicator, displaying the most recent portion of the 3D images on a portion of the display screen 20.

In some implementations, the method 600 further includes displaying time series of 3D images on a portion of the display screen 20.

In some implementations, the method 600 further includes displaying a 2D projection function on the user interface, for viewing 2D sections of the 3D images at a specified plane, and in response to receiving user input selecting the 2D projection function, displaying the 2D sections on a portion of the display screen 20.

In some implementations, the method 600 further includes displaying time series of the 2D sections on a portion of the display screen 20.

In some implementations, the method 600 further includes displaying a capture graphical indicator on the user interface, for capturing one of the ultrasound images displayed on the display screen 20, in response to receiving user input selecting the capture graphical indicator, storing currently displayed image as a captured image, saving the captured image to a database 40, and displaying a thumbnail of the captured image in a gallery on the user interface, for current examination.

In some implementations, the method 600 further includes displaying a plurality of thumbnails of a plurality of captured images in the gallery on the user interface; and in response to receiving user input selecting one of the plurality of thumbnails in the gallery, displaying the corresponding captured image on a portion of the display screen 20 for current examination.

In some implementations, the displayed captured image is from a 2D scan. In some implementations, the method 600 further comprises: displaying time series of 2D images on a portion of the display screen 20.

In some implementations, the displayed captured image is from a 3D scan. In some implementations, the method 600 further includes displaying time series of 3D images on a portion of the display screen 20.

In some implementations, the method 600 further includes displaying a 2D projection function on the user interface, for viewing 2D sections of the 3D images at a specified plane; and in response to receiving user input selecting the 2D projection function, displaying the 2D sections on a portion of the display screen 20.

In some implementations, the method 600 further includes displaying time series of the 2D sections on a portion of the display screen 20.

In some implementations, the display screen 20 is on a mobile device.

In some implementations, receiving ultrasound images further includes importing the active ultrasound image to a touchpad on the user interface, wherein by tapping on the lesion on the touchpad, a relative depth of the lesion in an image frame of the anatomical feature is captured.

Figure 7:
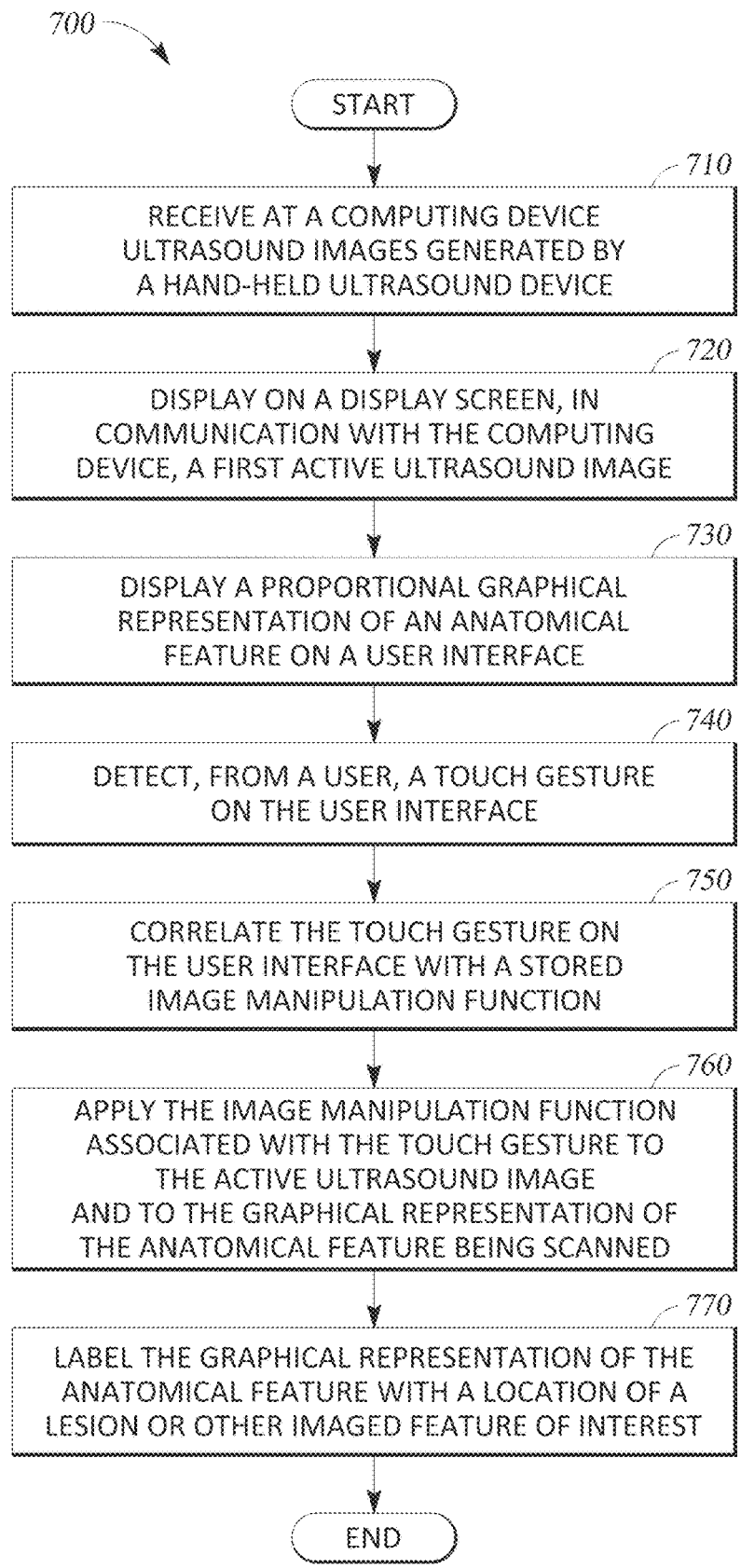
FIG. 7 is a process flow diagram illustrating an example method for labeling ultrasound images.

FIG. 7 illustrates an example flowchart depicting a method 700 for labeling ultrasound images, in accordance with embodiments described above. Although the method 700 is illustrated in a particular order, the steps may be performed in a different order, or omitted, altered, additional steps can be added or any combination of these are possible. Other process flows are possible.

The method 700 moves from a start state to block 710 of receiving at a computing device 30 ultrasound images generated by a hand-held ultrasound device 10. The method 700 then moves to block 720 of displaying on a display screen 20, in communication with the computing device 30, a first active ultrasound image. The method 700 then continues to block 730, displaying a proportional graphical representation of an anatomical feature on a user interface comprising a touch-screen, the displayed graphical representation being displayed separately from the first active ultrasound image displayed on the first device display screen 20. The method 700 then moves to block 740 where it detects, a touch gesture input from a user on the user interface. The method 700 then moves to block 750 where it correlates the touch gesture on the user interface with a stored image manipulation function. Each of a plurality of touch gestures can be correlated to a different image manipulation function. The method 700 then moves to block 760 where it applies the image manipulation function associated with the touch gesture to the active ultrasound image and to the graphical representation of the anatomical feature being scanned, and information associated with the touch gesture on the user interface manipulates the active ultrasound image. The method 700 then moves to block 770, labeling the graphical representation of the anatomical feature with a location of a lesion or other imaged feature of interest. A label applied to the graphical representation of the anatomical feature on the user interface can appear on the active ultrasound image that is being displayed on the display screen 20. In some implementations, subsequent touch gestures on the user interface modify the label of the lesion on the displayed active ultrasound image.

Ultrasound Image Acquisition, Visualization, and Processing

In phased array ultrasonics, a plurality of acoustic pulses (pulse) may be communicated from a plurality of transducers in fractions of a second and the returning wave fronts may be captured to rapidly create a series of image frames that can be displayed in real time. The pulses may be communicated from some or all of the transducers in the phased array at one time. In some embodiments, all of the transducers send a pulse at once. In other embodiments, groups of transducers in the phased array may send pulses at the same time. In some embodiments, the reflected wave front from a pulse may be time-shifted to compensate for varying delays based on the position of the transducer relative to other transducers pulsing at the same time. Each set of pulses from a phased array may be sent at the same or one or more different frequencies. In some embodiments, each set of pulses from the phased array may be of the same frequency. For example, a first pulse may be communicated at one frequency. A subsequent pulse may be communicated at a different frequency. In some embodiments, such differences in frequency may be optimized to allow for the capture of the highest quality image at a particular depth. Samples of the returning wave front may be captured at a plurality of time fractions (Q-block) from which the depth of penetration of the signal may be calculated.

A pulse communicated by a transducer may be reflected back to the transducer after striking a reflector such as a change in acoustic impedance. The transducer receives the returning echoes and captures fractions, based on the sampling rate of analog-to-digital converters of at least 2 times to about 4 times, about 6 times, about 7 times, or about 10 times, the fundamental acoustic pulse frequency or any subset thereof. The echoes may be converted to samples by the analog to digital converter in the transducer which generates a specific number of bits of data per sample, for example 12 bits/sample. A plurality of sample data from within a first time fraction of the echo forms a quantum block (Q-block) of the data. Each sample of data (data captured from a specific moment in time) from each transducer may be sent to a buffer dedicated to that transducer, and the processed data from fractions of fractions (sampling of Q-blocks) may be collected into one coherent Q-block which is then transmitted to a central processing unit. Once the echoes from a first pulse have sufficiently attenuated, a second pulse may be generated from the transducers and samples from a second Q-block of time of the echo may be buffered. The echoes may be allowed to attenuate and a third pulse may be generated from the transducers and samples from a third time fraction of the echo may be buffered. The echoes may be allowed to die and a pulse may be generated n times until the time fraction of the captured echo in an nth Q block reaches maximum attenuation or amplitude decay. In some embodiments, each Q-block may capture an independent depth as a function of time so that each Q-block is from an adjacent depth as represented by a consecutive lengths of time (t) during which a pulse is communicated and an echo returns. In other embodiments, one or more Q-blocks may overlap in the same or different amounts of depth increasing the likelihood that an object of interest may be fully imaged in a single Q-block maintaining phase coherence and therefore increasing image quality. In additional embodiments, Q-blocks may overlap more at the edges and corners and less in the middle curving the upper and lower edges of a Q-block and maximizing the quality of the final image while still restricting the amount of memory needed in the buffer. Q-blocks may overlap by about 0% to about 50% or any fraction thereof with the previous and/or subsequent Q-block.

While the fractions of time making up each Q-block may be any amount of time desired, each fraction may be small enough to implement locally to the front end circuitry and large enough for coherent signal analysis such that there is coherent data from all transducers in a given reflected wave front and the Q-blocks can be reassembled into a consistent image after processing. In some embodiments the fraction may be at least about four times the analog to digital sample times (where depth is measured in relation to time) to a maximum of the entire image volume of a single q-block.

The data from each Q-block may be transmitted at a rate greater than the peak data generation rate to a buffer in which each transducer has dedicated memory. The size of the buffer in the memory cache may be the same or different for each transducer. In some embodiments, the size of the buffer may be larger for transducers located on the edges of the phased array. In some embodiments, the buffer transmits the data from the first time fraction through a standard interface to a central processing unit. While the data from the first time fraction is being transferred, the digital signal from a second or subsequent time fraction fills the buffer. In some embodiments, each subsequent time fraction fills the buffer as the prior time fraction is transferred to a central processing unit. The central processing unit then assembles the Q-blocks of time into a single image frame. In some embodiments, the central processing unit waits until all time fractions have been received. In other embodiments, the central processing unit assembles the time fractions as they are received. In additional embodiments, the central processing unit assembles the Q-blocks for a previous image frame while receiving a digital signal for a subsequent image frame. If the Q-blocks overlap, the image may be averaged as images are not restricted to phase coherence. The process may be repeated for each frame, beginning again with a first Q-block.

Images from a phased array may be created by interpreting the intensity of the reflected echoes. In order to distinguish between different objects, different objects must have different resistances to sound (acoustic impedance) (Z) where Z=density×velocity. As sound passes through tissue, each tissue attenuates the sound at a different rate. Attenuation increases with depth and the higher the frequency of the pulse, the more rapidly a signal will attenuate. However, the higher the frequency of the pulse, the better the image quality. In some embodiments, the frequency of the pulse may be altered between subsequent pulses to obtain the best image for each depth captured by a Q-block of time.

When a wave passes from one type of tissue to another, the frequency is constant, but because the velocity changes (velocity (v)=wavelength (λ)×frequency (f)), the wavelength also changes. By comparing the attenuation length to the wavelength, the maximum frequency at which ultrasound can coherently propagate in a statistical fluid can be estimated. Every material has an attenuation coefficient, a quantity that characterizes how easily a material can be penetrated by energy. The attenuation coefficient can be defined as $\alpha = 20 \log_{10}(e)(\mu_A) \approx 8.7 \mu_A$ where $\mu_A$ is the amplitude attenuation factor in $cm^{-1}$ and e is Napier's constant (about 2.71828). Attenuation is determined by α[dB/(MHz*cm)]*total distance traveled[cm]*f[MHz]. Attenuation may also be quantified as a measure of the distance a pulse travels before its amplitude is attenuated to ½ its original value. Typical values for the attenuation coefficient in the human body may be about: fat 0.6 dB/cm*MHz, liver 0.5-0.94, kidney 1.0 dB/cm*MHz, muscle 1.3-3.3 dB/cm*MHz, bone 20 dB/cm*MHz and air 12 dB/cm*MHz resulting in average sound speeds in meters (m)/second (s) of 1540 m/s in soft tissue, 1459 m/s in fat, 1570 m/s in blood and 4080 m/s in bone (Feigenbaum's Echocardiography, 6th Edition, 2005, Lippincott Williams & Wilkins). Attenuation may additionally be caused by the angle of a returning wave front. Such an attenuation is proportional to the cosine of the angle of the wave front to normal. For example, a wave reflected at a 45° angle may lose 3 dB in amplitude in addition to any tissue attenuation.

The depth to which a pulse can usefully penetrate can be calculated by d=(v×time (t))/2, where time is the time it takes for a pulse to travel from a transducer to the reflection point and then from the reflection point back to the transducer. For example for soft tissue, a pulse intersecting with an object of interest at a depth of 1 cm would return a wave front in 13μ seconds. Maximum useful depth can also be calculated as (amplitude of signal)/(2*(frequency)) in centimeters. For example, with a standard transducer amplitude of ~65 dB, a frequency of 2.5 MHz would penetrate about 13 centimeters, appropriate for imaging the deep abdomen, whereas a frequency of 10 MHZ would penetrate only about 3.25 cm, appropriate for imaging the breast, thyroid, superficial veins or masses. The higher the frequency, the greater the image resolution and the greater the rate and amount of data produced per unit of time.

The disclosed system and method may be used for annotating an ultrasound image frame in an active ultrasound scan. The disclosed system may comprise a first display device and a control device with a touch screen user interface. In some embodiments, the system may further comprise ancillary devices such as, but not limited to, a keyboard, mouse, track ball and the like. In some embodiments, the ultrasound image on the first display device may be optimized using optimization controls on the user interface including, but not limited to, focal zone, time gain compensation, dynamic range, frame rate, Doppler gain, and field width. The control device displays a proportional graphical representation of the anatomical feature being scanned. By interacting with the graphical representation of the anatomical feature, labels and other information may be placed on an ultrasound image in the active ultrasound scan on the first display device. Interactions with the graphical representation of the anatomical feature comprise a touch gesture on the user interface with a stored image manipulation function such that each type of touch gesture may be correlated to a different image manipulation function and applies the image manipulation function to the ultrasound image and/or the graphical representation of the anatomical feature being scanned. Such information may include, but is not limited to, the presence of a lesion, the size of the lesion, the location of a lesion, type of lesion, distance from anatomical landmarks, transducer direction and the like. The label applied to the ultrasound image may be entered using a gesture, chosen from a word bank, chosen from a set of structure labels, or entered manually through the use of a touch screen or ancillary keyboard. In some embodiments, subsequent touch gestures on the user interface modify the label of the lesion on the displayed active ultrasound image.

In addition to an active ultrasound scan, thumbnails of images from prior generated scans from one or more prior studies and images from the current scans of the anatomical feature under examination may be displayed on the first display device. Such images may be manipulated by actions on the user interface and/or through interaction with an ancillary device.

In some embodiments, the active ultrasound image may be reproduced on a touchpad surface on the user interface. By interacting with the touchpad surface, the relative depth of the lesion in the anatomical feature being scanned may be captured.

The information placed on the active ultrasound image and/or the graphical representation of the anatomical feature being scanned may be captured in a worksheet. Such a worksheet may be used to provide a reference for the individual reviewing the ultrasound or may be produced as a final report ready for signature by the individual reviewing the ultrasound.

In some embodiments, a computer operated method of running a visualization application on the computer to compare prior generated images of an anatomical feature during an active scan may include displaying patient information on a first device that has been inputted through a user interface, receiving an input of the anatomical feature, retrieving a series of prior generated ultrasound images of the anatomical feature, determining the ultrasound images matching the labels from the prior generated worksheet from the series of prior generated ultrasound images of the anatomical feature, displaying a graphical representation of the anatomical feature on the user interface, populating the graphical representation of the anatomical feature with labels from a prior generated worksheet, marking a lesion matching the labels from the prior generated worksheet on the active scan, and/or comparing changes in the anatomical feature. In some embodiments, the imported labels on the graphical representation may be modified to indicate the current labels on the active scan. The changes include, but are not limited to, additional lesions, change in size, and change in composition of prior lesions.

An ultrasound system may include an ultrasound probe, a first processor configured to form an ultrasound image from the ultrasound data, a first display screen divided into a group of sectors, each sector displaying different information, a touch-screen user interface, and/or a second processor that receives input from the touch-screen user interface. The ultrasound probe may include a transducer configured to transmit an ultrasound signal to a target object, receive an ultrasound echo signal reflected from the target object, and form ultrasound data corresponding to the target object.

In some embodiments, in response to receiving input from the touch-screen user interface, the second processor sends a signal to a labeling module to input labels and measurements of the target object on an image on the first display screen and a graphical representation of the anatomical feature on a user interface.

Information in the sectors of the first display screen may include, but are not limited to, the information in an active scan, captured images from the active scan, and images from previous scans of a same anatomical feature of a same individual.

The touch-screen user interface may include a graphical representation of an anatomical feature, a track pad, a keyboard, a word bank (a list of context-specific labels which are commonly used for a specific scan type or body part), a structured label bank ("structured labels" refers to a list of labels used for a specific exam type in which the labels are automatically presented in a set order), image optimization controls, and a series of drop-down menus with additional control options. In some embodiments, the touch-screen user interface may further include a measuring apparatus that calculates a distance between two fingers placed on the measuring apparatus and places a measurement for an anatomical feature on a label on the ultrasound image. In some embodiments, the labels applied to the active ultrasound image may appear at a comparable location on the graphical representation of the anatomical feature.

The disclosed ultrasound imaging system may be used for recording, comparing, labeling, reporting and/or documenting information received from an ultrasound probe. Further provided is a system including an ultrasound probe comprising a transducer configured to transmit an ultrasound signal to a target object, receive an ultrasound echo signal reflected from the target object, and form ultrasound data corresponding to the target object. The system may include a first processor configured to form an ultrasound image from the ultrasound data; a first display screen; a user interface including a touch-screen and a second processor that receives input from the user interface. A plurality of activation areas on the user interface allow for interaction with one or more ultrasound images and diagrams on the first display screen and the user interface. In some embodiments, the first and second processor may be a single processor. A labeling module may be activated by the user interface to add the appropriate labels to the active ultrasound image and to a graphical representation of the target object. A computer visualization application operated via the user interface allows for the manipulation and comparison of data on both the first display and the user interface.

The first display screen may be any type of screen device including a tablet, touchscreen, flat screen, LED screen, electroluminescent display, organic LED, LCD, virtual display and the like. The first display may present information in a variety of ways. In some embodiments, the first display screen may be divided into a plurality of sectors in any order each of which may contain one or more of: the patient information, the active ultrasound image being currently acquired from a machine transformation of an ultrasound reading in process (active scan), thumbnails of prior studies including studies performed on machines other than ultrasound machines, and thumbnails of recorded images from the current exam. In some embodiments, the thumbnails may be presented in chronological order. In other embodiments, the thumbnails may be presented in an order chosen by the user. Each thumbnail image may be expanded, moved, or removed as desired using gestures on the user interface. In some embodiments, the thumbnails may be stacked one on top of each other with the most recent scan on top. In other embodiments, thumbnails may be presented in discrete rows. Thumbnails may be labeled with the date and time of the scan as well as any other relevant label or descriptive information including, but not limited to, patient information, scan location, scan date, scan plane, anatomical subject of the scan, presence or absence of lesions, purpose of the scan, measurements of lesions, number of lesions and the like.

The content of the first display may be controlled by a user interface such as a touch-screen user interface that allows the user to manipulate the images on the first display. Touch-screen based computers comprise computer assemblies combining an internal computer processor and touch sensitive digital display screen. They commonly also have access to cloud based storage and computing support and wireless connectivity and may include voice recognition. The digital display and the computer's ability to monitor the positions and motions of finger touches on the touch-screen may be coordinated such that finger contact locations can be correlated by the computer with the information displayed at those locations. A variety of gestures may be used to interact with the user interface, including, but not limited to, touching, swiping, double tap, multiple finger taps, pinch, multi-touch, radio buttons and the like. A processor may be coupled to the touch-screen for detecting a touch by the user on the touch-screen that identifies a selected activation area. The processor then performs the device function associated with the stored image manipulation function thereby activating the selected activation area. In some embodiments, the user may interact with the user interface through voice recognition, a stylus, keyboard, mouse, virtual reality headset, hand gestures in the air, any other way generally used to interact with a user interface, or a combination thereof. In some embodiments, controls on the ultrasound probe may be used to input information onto either or both the user interface and the display screen. The IMU value of an ultrasound scanner may include the orientation and position angles of the scanner measured by an accelerometer in the scanner. The IMU value may be used to assign or associate a relative spatial position and orientation to each individual image. In some embodiments, the relative spatial position and orientation of each individual image may be used in generating a tomography. In some embodiments, the relative spatial position and orientation of each individual image may be used in generating 2D projections of 3D images.

The touch-screen user interface may be divided into a plurality of control sectors including, but not limited to, a proportionate graphical representation of the anatomical part being scanned, a scale or other measuring apparatus, a track pad, a series of one or more virtual controls such as buttons or radio buttons, word bank, structured label bank, tabbed drop down menus, virtual keyboard, active ultrasound image, virtual trackpad, virtual depth and focus sliders, virtual cine slider, and virtual time gain compensation sliders. In some embodiments, the number and arrangement of control sectors may be altered to suit the needs of the user. For example, during a scan, it may be desirable to have an extended display of one or more of the control sectors. In some embodiments, there may be one control sector. In other embodiments, there may be 2, 3, 4, 5, 6, 7, 8, 9, 10, 11, 12 or more control sectors. Activation of each sector on the user interface performs a function on the user interface and manipulates information on the first display screen and/or the user interface. In some embodiments, information may be entered by using a physical keyboard.

Patient information may be input through the touch-screen. In some embodiments, patient information may be part of a database that is part of the ultrasound imaging system. In other embodiments, patient information and prior scans may be retrievable from a network based database. For example, in a hospital, there is a typically a network-attached server that stores patient information, images and image acquisition settings such that they can be accessed from imaging devices in different locations. Once patient information is inputted through the touch-screen display and the scan type is indicated, the visualization application on the touch-screen populates the touch-screen with a graphical representation of the location of the anatomical scan, and populates one or more of the word bank, structured label bank, and drop down menus with context-specific labels pertinent to the anatomical location. If prior scans have been performed, the display presents a list of prior scans that may be selected for comparison to images from the active scan. In some embodiments, the system may tag suggested comparison scans which can be accepted or rejected by the user.

Useful ultrasound images may require at least two labels: the anatomical region being imaged and the scan plane or transducer orientation. Additional information that may be included with an image includes, but is not limited to, measurements of an anatomical feature of interest including the longest horizontal diameter, the anteroposterior diameter, and the orthogonal horizontal; the location of the anatomical feature of interest in reference to anatomical landmarks (such as the chest wall); the type of lesion or anatomical feature of interest; the orientation of the lesion of interest; the location and depth of the lesion of interest and the like.

An anatomical feature of interest may include in its label whether it is transverse (TR) or longitudinal (LG) indicating the direction of the scan; whether the lesion is a cyst, mass, duct or blood vessel; whether it is located anterior to or posterior to an anatomical landmark; its size and the like. For example, in a breast ultrasound, an anatomical feature of interest may include in its label whether it is the right or left breast, the clock face location in the breast, whether the scan plane is radial (RAD), anti-radial (AR-ARAD), transverse (TR), longitudinal (LG), and/or descriptive labels such as whether the lesion is a cyst, mass, duct or blood vessel, whether it is located anterior to or posterior to an anatomical landmark such as the nipple or chest wall, the measurements and number of lesions, and the like.

In some embodiments, structured labels, a word bank, or keyboard for manual entry of a label may be used to add information to labels or to modify existing information on a label regarding the active scan. In some embodiments, labels for all body parts may be listed. In some embodiments, where there are a finite number of anticipated or commonly used labels for a specific anatomical feature, the labels may be listed in a word bank. For example a word bank for a breast study may include, but is not limited to, RAD, ARAD, SAG, TRAN, Axilla, Axillary tail, Subarcolar, Inframammary fold, Anterior Axillary line, Middle Axillary line, Posterior Axillary line, Palp, Palp area, Tract, Calcifications, Heel rock, Toe rock, Skin fascia, Chest wall, Lateral to, Medial to, Cyst, Foam cyst, FA, Mass, Halo, Typical, swirling echoes, and vessel. A word bank for a thyroid study may include, but is not limited to, Right, Left, SAG, TR, Isthmus, upper pole, mid gland, lower pole, Esophagus, Cyst, Cystic changes, Microcalcifications, Thyroid bed, and Lower pole obscured by clavicle. A word bank for a cervical node study may include, but is not limited to, Cyst, Cystic changes, Calcification, Microcalcifications, Hilar flow, Cortical flow, and Thyroid bed.

Structured labels may be used where a scan generally proceeds in a standard order and typical images may be acquired. Standardized labels may appear in order and the user merely accepts the labels. Common scan types for structured labeling would include, but are not limited to, obstetrics, abdomen, carotid, lower extremity venous among others. The order and the labels in the structured label list may be fixed or customizable. In some embodiments, structured labels for an obstetric scan for maternal and fetal anatomy may be customized to be presented in the order the sonographer usually scans. Labels may also include numbers indicating the presence of a plurality of lesions and providing reference tags for follow up studies of each lesion. In some embodiments, each lesion may be numbered automatically.

Identification labeling of the scan image on the display may occur by interacting in one or more ways with the touch-screen user interface. For example, in some embodiments, placement of the identification labels may occur by tapping on the graphical representation on the user interface. When a location is tapped, a marker may appear on the graphical representation showing the location of the tap on the drawing and a location label corresponding to the marker may appear on the displayed active ultrasound image. The position of a label on the graphical representation may be re-positioned by selecting and dragging it. A directional swipe on the graphical representation may provide the scan plane label for the active image on the first display. If multiple lesions are being documented, the tap on the graphical representation may add a lesion number to the label on the active scan. In some embodiments, the same labels may appear on the graphical representation and the active scan when the graphical representation may be manipulated. In other embodiments, different labels may appear on the graphical representation and the active scan. In further embodiments, some labels may appear on the graphical representation or the active scan, but not both. For example, transducer direction may be necessary for the ultrasound image, but may be less so for the graphical representation. In additional embodiments, a label placed on the active image may be copied on the matching location on the graphical representation. The annotated graphical representation may become part of a study and be used as a data summary and/or as part of a final report. In additional embodiments, indicating placement of a lesion on the graphical representation on the user interface will create a lesion number and will capture the measurements of the lesion. In some embodiments, the label may include one or more symbols indicating the type of lesion or anatomical part shown in the ultrasound. For example, there may be symbols for a mass, duct, vessel, cyst, malignancy, benign lesions, lymph nodes, and the like. Such symbols may be dragged, stretched, pinched, or otherwise manipulated to more closely resemble the placement, size and shape of the actual lesion.

In additional embodiments, smart comparisons of ultrasound images may be made. For example, a user may freeze a frame of the active scan and place identifying labels such as a location or body part on the image. In another embodiment, pattern recognition may be used to locate or help locate relevant comparison images. In some embodiments, available prior images may include a standard set of "normal" images that may be used for training purposes, or to provide a standard reference for identifying abnormalities in a scan.

Many ultrasound scans require one or more measurements. In some embodiments, such measurements may be taken manually by measuring the distance on the patient with the left thumb and forefinger and tapping with the spaced thumb and forefinger in a two finger gesture on a measuring device such as a scale or ruler on the user interface. The user interface measures the distance tapped and adds the measurement to the current scan. Such measurements may be appropriately placed by dragging the measurement to the correct spot on a label or in a graphical representation. In other embodiments, a caliper may appear on the current scan and the caliper may be dragged or otherwise manipulated to the correct distance. In further embodiments, it may be desirable to take a plurality of measurements in various directions. Such a plurality of measurements may be labeled by number or other relevant information. In some embodiments, the creation of two or more measurements may be used to generate an ellipse between the calipers on the screen. The size and shape of the ellipse may be modified using finger motions such as pinch and spread on the user interfaces so that the ellipse surrounds the anatomical feature being measured as closely as possible. In a Doppler scan, calipers may measure properties related to Doppler velocities. In some embodiments, calipers placed on a Doppler waveform perform velocity calculations and waveform tracing. In additional embodiments, measurements on the active scan may be copied to the appropriate place on the graphical representation.

The data from an ultrasound may be frequently preserved in a worksheet which generally contains the anatomical feature being scanned, patient identification, clinical indication, relevant clinical information, measurements, the graphical representation and any marks or labels on the graphical representation, and observations specific to the anatomical feature being scanned. Worksheets as described herein may additionally contain measurements from one or more prior scans increasing the ability to monitor the progression of a change in an anatomical feature. In some embodiments, the user may create a new blank worksheet based on the graphical representation or may import a worksheet from a prior scan. If it is a follow-up scan using an imported prior worksheet, the imported prior worksheet may be displayed on the user interface in lieu of a new blank graphical representation, along with prior labels, prior measurements and the dates of the scans. In some embodiments, prior data may be displayed in a different color or font than new information. In some embodiments, the user may then scan the anatomical feature, freeze an image and label the new images by tapping the appropriate location on the graphical representation and swiping the graphical representation to indicate transducer orientation. In other embodiments, the user may tap a target on the graphical representation and then scan to look for the lesion. The active image is then labeled using the information provided by the target location on the graphical representation. In some embodiments, when the active image is frozen, it then takes its label from the information provided from the prior scan by the target location on the graphical representation. These worksheets may be used to summarize data for a reader to use in compiling a report or may be signed as a final report.

Further exemplary methods and systems for ultrasound imaging and control, exemplary methods and apparatus for phased array ultrasonics, exemplary methods and apparatus for multi-zone, multi-frequency ultrasound imaging and reconstruction, exemplary methods and apparatus for thick-slice 3-dimensional ultrasound imaging, exemplary methods and apparatus for integration of 3- and 2-dimensional ultrasound imaging, exemplary methods and systems for capturing, labeling, measuring and comparing images from ultrasound studies, exemplary methods and systems of processing ultrasound images using a touch-screen user interface, and exemplary hand-held ultrasound devices are described in U.S. Patent Application Publication No. 2017/0307755 and 2018/0055483, U.S. Pat. Nos. 10,401,492 and 10,499,882, U.S. patent application Ser. Nos. 63/004,352, 63/004351, 63/004354, 29/689,849, 29/689,847 and 29/729,816, each of which is incorporated herein by reference in its entirety.

Implementation Considerations

References to "one embodiment" or "an embodiment" do not necessarily refer to the same embodiment, although they may. Unless the context clearly requires otherwise, throughout the description and the claims, the words "comprise," "comprising." and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple one. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other.

"Logic" refers to machine memory circuits, non-transitory machine readable media, and/or circuitry which by way of its material and/or material-energy configuration comprises control and/or procedural signals, and/or settings and values (such as resistance, impedance, capacitance, inductance, current/voltage ratings, etc.), that may be applied to influence the operation of a device. Magnetic media, electronic circuits, electrical and optical memory (both volatile and nonvolatile), and firmware are examples of logic. Logic specifically excludes pure signals or software per se (however does not exclude machine memories comprising software and thereby forming configurations of matter). Those skilled in the art will appreciate that logic may be distributed throughout one or more devices, and/or may be comprised of combinations of memory, media, processing circuits and controllers, other circuits, and so on. Therefore, in the interest of clarity and correctness logic may not always be distinctly illustrated in drawings of devices and systems, although it is inherently present therein.

The techniques and procedures described herein may be implemented via logic distributed in one or more computing devices. The particular distribution and choice of logic will vary according to implementation. Those having skill in the art will appreciate that there are various logic implementations by which processes and/or systems described herein can be effected (e.g., hardware, software, and/or firmware), and that the preferred vehicle will vary with the context in which the processes are deployed. "Software" refers to logic that may be readily readapted to different purposes (e.g. read/write volatile or nonvolatile memory or media). "Firmware" refers to logic embodied as read-only memories and/or media. Hardware refers to logic embodied as analog and/or digital circuits. If an implementer determines that speed and accuracy are paramount, the implementer may opt for a hardware and/or firmware vehicle; alternatively, if flexibility is paramount, the implementer may opt for a solely software implementation; or, yet again alternatively, the implementer may opt for some combination of hardware, software, and/or firmware. Hence, there are several possible vehicles by which the processes described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations may involve optically-oriented hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood as notorious by those within the art that each function and/or operation within such block diagrams, flowcharts, or examples can be implemented, individually and/or collectively, by a wide range of hardware, software, firmware, or virtually any combination thereof. Several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, flash drives, SD cards, solid state fixed or removable storage, and computer memory. In a general sense, those skilled in the art will recognize that the various aspects described herein which can be implemented, individually and/or collectively, by a wide range of hardware, software, firmware, or any combination thereof can be viewed as being composed of various types of "circuitry." Consequently, as used herein "circuitry" includes, but is not limited to, electrical circuitry having at least one discrete electrical circuit, electrical circuitry having at least one integrated circuit, electrical circuitry having at least one application specific integrated circuit, circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), circuitry forming a memory device (e.g., forms of random access memory), and/or circuitry forming a communications device (e.g., a modem, communications switch, or optical-electrical equipment).

Those skilled in the art will recognize that it is common within the art to describe devices and/or processes in the fashion set forth herein, and thereafter use standard engineering practices to integrate such described devices and/or processes into larger systems. That is, at least a portion of the devices and/or processes described herein can be integrated into a network processing system via a reasonable amount of experimentation.

The foregoing described aspects depict different components contained within, or connected with different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

One or more aspects or features of the subject matter disclosed or claimed herein (e.g., processes and methods) may be realized in digital electronic circuitry, integrated circuitry, specially designed application specific integrated circuits (ASICs), field programmable gate arrays (FPGAs) computer hardware, firmware, software, and/or combinations thereof. These various aspects or features may include implementation in one or more computer programs that may be executable and/or interpretable on a programmable system including at least one programmable processor, which may be special or general purpose, coupled to receive data and instructions from, and to transmit data and instructions to, a storage system, at least one input device, and at least one output device. The programmable system or computing system may include clients and servers. A client and server may be remote from each other and may interact through a communication network. The relationship of client and server arises by virtue of computer programs running on the respective computers and having a client-server relationship to each other.

These computer programs, which may also be referred to as programs, software, software applications, applications, components, or code, may include machine instructions for a programmable controller, processor, microprocessor or other computing or computerized architecture, and may be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium may store such machine instructions non-transitorily, such as for example as would a non-transient solid-state memory or a magnetic hard drive or any equivalent storage medium. The machine-readable medium may alternatively or additionally store such machine instructions in a transient manner, such as for example as would a processor cache or other random access memory associated with one or more physical processor cores.

In some embodiments, to provide for interaction with a user, one or more aspects or features of the subject matter described herein may be implemented on a computer having a display device for displaying information to the user, and an input interface by which the user may provide input to the computer. Other kinds of devices may be used to provide for interaction with a user as well. Other possible input devices include touch screens or other touch-sensitive devices such as single or multi-point resistive or capacitive trackpads, voice recognition hardware and software, and the like.

In some embodiments, to provide for interaction with a user, one or more aspects or features of the subject matter described herein may be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices may be used to provide for interaction with a user as well. For example, feedback provided to the user may be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive trackpads, voice recognition hardware and software, optical scanners, optical pointers, digital image capture devices and associated interpretation software, and the like.

Many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Various embodiments of the present disclosure may be a system, a method, and/or a computer program product at any possible technical detail level of integration. The computer program product may include a computer readable storage medium (or mediums) having computer readable program instructions thereon for causing a processor to carry out aspects of the present disclosure.

For example, the functionality described herein may be performed as software instructions executed by, and/or in response to software instructions being executed by, one or more hardware processors and/or any other suitable computing devices. The software instructions and/or other executable code may be read from a computer readable storage medium (or mediums).

The computer readable storage medium can be a tangible device that can retain and store data and/or instructions for use by an instruction execution device. The computer readable storage medium may be, for example, but is not limited to, an electronic storage device (including any volatile and/or non-volatile electronic storage devices), a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a solid state drive, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions (as also referred to herein as, for example, "code," "instructions," "module," "application." "software application," and/or the like) for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Java, C++, or the like, and procedural programming languages, such as the "C" programming language or similar programming languages. Computer readable program instructions may be callable from other instructions or from itself, and/or may be invoked in response to detected events or interrupts. Computer readable program instructions configured for execution on computing devices may be provided on a computer readable storage medium, and/or as a digital download (and may be originally stored in a compressed or installable format that requires installation, decompression or decryption prior to execution) that may then be stored on a computer readable storage medium. Such computer readable program instructions may be stored, partially or fully, on a memory device (e.g., a computer readable storage medium) of the executing computing device, for execution by the computing device. The computer readable program instructions may execute entirely on a user's computer (e.g., the executing computing device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to methods, apparatus (systems), and computer program products according to embodiments of the disclosure. It will be understood that each method can be implemented by computer readable program instructions. These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart(s) and/or block diagram(s) block or blocks.

The technology described herein illustrates certain architecture, functionality, and operation of possible implementations of systems, methods, and computer program products according to various embodiments of the present disclosure. In this regard, the functionality can be implemented in software or hardware. The functionality can be implemented by special purpose hardware-based systems that perform the specified functions or acts or carry out combinations of special purpose hardware and computer instructions. For example, any of the processes, methods, algorithms, elements, blocks, applications, or other functionality (or portions of functionality) described in the preceding sections may be embodied in, and/or fully or partially automated via, electronic hardware such application-specific processors (e.g., application-specific integrated circuits (ASICs)), programmable processors (e.g., field programmable gate arrays (FPGAs)), application-specific circuitry, and/or the like (any of which may also combine custom hard-wired logic, logic circuits, ASICs, FPGAs, etc. with custom programming/execution of software instructions to accomplish the techniques).

Any of the above-mentioned processors, and/or devices incorporating any of the above-mentioned processors, may be referred to herein as, for example, "computers." "computer devices." "computing devices," "hardware computing devices," "hardware processors." "processing units," and/or the like.

It will also be understood that, when a feature or element is referred to as being "connected", "attached" or "coupled" to another feature or element, it may be directly connected, attached or coupled to the other feature or element or intervening features or elements may be present. In contrast, when a feature or element is referred to as being "directly connected", "directly attached" or "directly coupled" to another feature or element, there may be no intervening features or elements present. Although described or shown with respect to one embodiment, the features and elements so described or shown may apply to other embodiments.

Terminology used herein is for the purpose of describing particular embodiments and implementations only and is not intended to be limiting. For example, as used herein, the singular forms "a", "an" and "the" may be intended to include the plural forms as well, unless the context clearly indicates otherwise. It will be further understood that the terms "comprises" and/or "comprising." when used in this specification, specify the presence of stated features, steps, operations, processes, functions, elements, and/or components, but do not preclude the presence or addition of one or more other features, steps, operations, processes, functions, elements, components, and/or groups thereof. As used herein, the term "and/or" includes any and all combinations of one or more of the associated listed items and may be abbreviated as "/".

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on." such that an un-recited feature or element is also permissible.

Spatially relative terms, such as "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features due to the inverted state. Thus, the term "under" may encompass both an orientation of over and under, depending on the point of reference or orientation. The device may be otherwise oriented (rotated 90 degrees or at other orientations) and the spatially relative descriptors used herein interpreted accordingly. Similarly, the terms "upwardly", "downwardly", "vertical", "horizontal" and the like may be used herein for the purpose of explanation only unless specifically indicated otherwise.

As used herein in the specification and claims, including as used in the examples and unless otherwise expressly specified, all numbers may be read as if prefaced by the word "about" or "approximately." even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise.

For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, may represent endpoints or starting points, and ranges for any combination of the data points. For example, if a particular data point "10" and a particular data point "15" may be disclosed, it is understood that greater than, greater than or equal to, less than, less than or equal to, and equal to 10 and 15 may be considered disclosed as well as between 10 and 15. It is also understood that each unit between two particular units may be also disclosed. For example, if 10 and 15 may be disclosed, then 11, 12, 13, and 14 may be also disclosed.

Although various illustrative embodiments have been disclosed, any of a number of changes may be made to various embodiments without departing from the teachings herein. For example, the order in which various described method steps are performed may be changed or reconfigured in different or alternative embodiments, and in other embodiments one or more method steps may be skipped altogether. Optional or desirable features of various device and system embodiments may be included in some embodiments and not in others. Therefore, the foregoing description is provided primarily for the purpose of example and should not be interpreted to limit the scope of the claims and specific embodiments or particular details or features disclosed.

The examples and illustrations included herein show, by way of illustration and not of limitation, specific embodiments in which the disclosed subject matter may be practiced. As mentioned, other embodiments may be utilized and derived therefrom, such that structural and logical substitutions and changes may be made without departing from the scope of this disclosure. Such embodiments of the disclosed subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve an intended, practical or disclosed purpose, whether explicitly stated or implied, may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The disclosed technology has been provided here with reference to one or more features or embodiments. Those skilled in the art will recognize and appreciate that, despite of the detailed nature of the example embodiments provided here, changes and modifications may be applied to said embodiments without limiting or departing from the generally intended scope. These and various other adaptations and combinations of the embodiments provided here are within the scope of the disclosed subject matter as defined by the disclosed elements and features and their full set of equivalents.

What is claimed is:

1. A method for visualizing two-dimensional (2D), three-dimensional (3D), and four-dimensional (4D) ultrasound images generated by a hand-held ultrasound device during an active scan, the method comprising:
   receiving, during an active scan, 3D ultrasound images generated by a hand-held ultrasound device;
   displaying the 3D ultrasound images on a unitary touch screen user interface configured to display the ultrasound images in a first display state;
   displaying a display state selection on the unitary touch screen user interface in communication with a computing device, the display state selection indicating to receive 2D images;
   receiving position data from an inertial sensor in the hand-held ultrasound device;
   determining orientation and position angles of the hand-held ultrasound device based on the position data;
   receiving a display state selection from a user on the unitary touch screen user interface indicating to generate 2D ultrasound images of a specified plane of the 3D ultrasound images;
   in response to receiving the display state selection indicating to generate 2D ultrasound images, controlling the hand-held ultrasound device to generate, during the active scan, 2D ultrasound images of the specified plane based on the orientation and the position angles of the hand-held ultrasound device and communicate the generated 2D ultrasound images to the computing device;
   displaying the generated 2D ultrasound images in the selected display state on a portion of the unitary touch screen user interface,
   in response to displaying the generated 2D ultrasound images, displaying, on the unified touch screen user interface, a contextual action selection overlaid on the unitary touch screen interface, wherein the contextual action selection corresponds to transformations available 2D ultrasound images.

2. The method of claim 1, wherein generating ultrasound images comprises generating 2D images, and wherein the method further comprises:
   displaying a capture graphical indicator on the unitary touch screen user interface, for capturing one of the 2D images displayed on the unitary touch screen user interface; and
   in response to receiving user input selecting the capture graphical indicator, storing currently displayed 2D image.

3. The method of claim 1, wherein generating ultrasound images comprises generating 3D images, and wherein the method further comprises:
   displaying a capture graphical indicator on the unitary touch screen user interface, for capturing one of the 3D images displayed on the unitary touch screen user interface; and
   in response to receiving user input selecting the capture graphical indicator, storing currently displayed 3D image.

4. The method of claim 1, wherein generating ultrasound images comprises generating 2D images, and wherein the method further comprises:
   displaying a 2D frozen review graphical indicator on the unitary touch screen user interface, for reviewing a most recent portion of the 2D images generated by the hand-held ultrasound device; and in response to receiving user input selecting the 2D frozen review graphical indicator, displaying the most recent portion of the 2D images on a portion of the unitary touch screen user interface.

5. The method of claim 4, further comprising displaying time series of 2D images on a portion of the unitary touch screen user interface.

6. The method of claim 1, wherein generating ultrasound images comprises generating 3D images, and wherein the method further comprises:

displaying a 3D frozen review graphical indicator on the unitary touch screen user interface, for reviewing a most recent portion of the 3D images generated by the hand-held ultrasound device; and in response to receiving user input selecting the 3D frozen review graphical indicator, displaying the most recent portion of the 3D images on a portion of the unitary touch screen user interface.

7. The method of claim 6, further comprising displaying time series of 3D images on a portion of the unitary touch screen user interface.

8. The method of claim 6, wherein the method further comprises:

displaying a 2D projection function on the unitary touch screen user interface, for viewing 2D sections of the 3D images at a specified plane; and in response to receiving user input selecting the 2D projection function, displaying the 2D sections on a portion of the unitary touch screen user interface.

9. The method of claim 8, further comprising displaying time series of the 2D sections on a portion of the unitary touch screen user interface.

10. The method of claim 1, wherein the method further comprises:

displaying a capture graphical indicator on the unitary touch screen user interface, for capturing one of the ultrasound images displayed on the unitary touch screen user interface;

in response to receiving user input selecting the capture graphical indicator, storing currently displayed image as a captured image;

saving the captured image to a database; and displaying a thumbnail of the captured image in a gallery on the unitary touch screen user interface, for current examination.

11. The method of claim 10, wherein the method further comprises:

displaying a plurality of thumbnails of a plurality of captured images in the gallery on the touch screen user interface; and in response to receiving user input selecting one of the plurality of thumbnails in the gallery, displaying the corresponding captured image on a portion of the unitary touch screen user interface for current examination.

12. The method of claim 11, wherein the displayed captured image is from a 2D scan, and wherein the method further comprises:

displaying time series of 2D images on a portion of the unitary touch screen user interface.

13. The method of claim 11, wherein the displayed captured image is from a 3D scan, and wherein the method further comprises:

displaying time series of 3D images on a portion of the unitary touch screen user interface.

14. The method of claim 13, wherein the method further comprises:

displaying a 2D projection function on the unitary touch screen user interface, for viewing 2D sections of a 3D image from the 3D scan at a specified plane; and in response to receiving user input selecting the 2D projection function, displaying the 2D sections of the 3D image on a portion of the unitary touch screen user interface.

15. The method of claim 14, further comprising displaying time series of the 2D sections on a portion of the unitary touch screen user interface.

16. The method of claim 1, wherein the unitary touch screen user interface is on a mobile device.

17. The method of claim 1, further comprising displaying a received ultrasound image on the unitary touch screen user interface, receiving a user input on a lesion in the displayed ultrasound image, and determining a relative depth of the lesion in an image frame of the anatomical feature is captured.

* * * * *